US 12,173,367 B2

(12) United States Patent
Aliado et al.

(10) Patent No.: US 12,173,367 B2
(45) Date of Patent: Dec. 24, 2024

(54) ELECTRICAL ENHANCEMENT OF BILAYER FORMATION

(71) Applicant: Roche Sequencing Solutions, Inc., Pleasanton, CA (US)

(72) Inventors: Kevin Aliado, Sunnyvale, CA (US); Roger J. A. Chen, Saratoga, CA (US); Jing Luo, Daly City, CA (US); J. William Maney, Jr., Emerald Hills, CA (US); William Nielsen, San Jose, CA (US); Kyle Umeda, Saratoga, CA (US); Ashraf Wahba, Hayward, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 18/482,807

(22) Filed: Oct. 6, 2023

(65) Prior Publication Data

US 2024/0035083 A1    Feb. 1, 2024

Related U.S. Application Data

(60) Continuation of application No. 17/304,455, filed on Jun. 21, 2021, now Pat. No. 11,814,676, which is a
(Continued)

(51) Int. Cl.
*G01N 33/48* (2006.01)
*C12Q 1/6869* (2018.01)
*G01N 33/487* (2006.01)

(52) U.S. Cl.
CPC ..... *C12Q 1/6869* (2013.01); *G01N 33/48721* (2013.01)

(58) Field of Classification Search
CPC ........ G01N 33/4872; G01N 27/3278
See application file for complete search history.

(56) References Cited

U.S. PATENT DOCUMENTS

| 6,015,714 A | 1/2000 | Baldarelli et al. |
| 8,828,208 B2 | 9/2014 | Canas et al. |

(Continued)

FOREIGN PATENT DOCUMENTS

| CN | 102405410 A | 4/2012 |
| CN | 105273991 A | 1/2016 |

(Continued)

OTHER PUBLICATIONS

Goldstein et al., CMOS Low Current Measurement System for Biomedical Applications, IEEE Transactions on Biomedial Circuits and Systems, Apr. 2012, pp. 111-119, vol. 6, No. 2.
(Continued)

*Primary Examiner* — Cachet I Proctor
(74) *Attorney, Agent, or Firm* — FisherBroyles, LLP; Jason M. Pass; Frank W. Leak, Jr.

(57) ABSTRACT

A method of forming a plurality of lipid bilayers over an array of cells in a nanopore based sequencing chip is disclosed. Each of the cells comprises a well. A salt buffer solution is flowed over the array of cells in the nanopore based sequencing chip to substantially fill the wells in the cells with the salt buffer solution. A lipid and solvent mixture is flowed over the array of cells to deposit the lipid and solvent mixture over at least some of the wells in the cells. A first portion of the cells, each having a lipid bilayer over its well, is detected. A second portion of the cells, each having a lipid membrane but not a lipid bilayer over its well, is detected. An electrical lipid-thinning stimulus is selectively applied to the second portion of the cells but not to the first portion of the cells.

18 Claims, 16 Drawing Sheets

Related U.S. Application Data continuation of application No. 16/578,189, filed on Sep. 20, 2019, now Pat. No. 11,041,198, which is a division of application No. 15/085,713, filed on Mar. 30, 2016, now Pat. No. 10,465,240.

(56) References Cited

U.S. PATENT DOCUMENTS

| | | | |
|---|---|---|---|
| 9,605,307 | B2 | 3/2017 | Chen et al. |
| 9,678,055 | B2 | 6/2017 | Chen et al. |
| 10,471,429 | B2 | 11/2019 | Noji et al. |
| 2010/0019620 | A1 | 1/2010 | Kastl et al. |
| 2012/0296230 | A1* | 11/2012 | Davis ............... A61B 5/24 606/129 |
| 2013/0048499 | A1 | 2/2013 | Mayer et al. |
| 2014/0034497 | A1* | 2/2014 | Davis ............... G01N 27/44791 438/689 |
| 2014/0203464 | A1 | 7/2014 | Chen et al. |
| 2015/0153302 | A1* | 6/2015 | Davis ............... C12Q 1/6869 204/403.08 |
| 2015/0275287 | A1 | 10/2015 | Tian |
| 2015/0337366 | A1 | 11/2015 | Davis et al. |

FOREIGN PATENT DOCUMENTS

| | | |
|---|---|---|
| JP | 2011506994 A | 3/2011 |
| JP | 2015508896 A5 | 1/2016 |
| JP | 2015525077 A5 | 7/2016 |
| JP | 2015040754 A5 | 9/2016 |
| WO | 2009/024775 A1 | 2/2009 |
| WO | 2009077734 A2 | 6/2009 |
| WO | 2010122293 A1 | 10/2010 |
| WO | 2011097028 A1 | 8/2011 |
| WO | 2013/123450 A1 | 8/2013 |
| WO | 2013188841 A1 | 12/2013 |
| WO | 2015061510 A1 | 4/2015 |

OTHER PUBLICATIONS

Gross et al., "Determining membrane capacitance by dynamic control of droplet interface bilayer area", Langmuir, 2011, 27(23):14335-42.

International Preliminary Report on patentability issued in corresponding PCT application PCT/E P2017/057428, 2017.

International Search Report mailed on Jun. 6, 2017 in corresponding PCT application No. PCT/EP2017/057428 filed on Mar. 29, 2017.

Louis Paul Hromada, "Bllyer lipid membrane (BML) integration into Microfluidic Platforms with Application Toward BML-Based Biosensors" Graduate School of the university of Maryland, College Park, 2007, pp. 1-206.

N/A, Planar lipid bilayer electrophysiology, Krantz Lab, 2012, http://mcb.berkeley.edu/labs/krantz/equipment/blm.html (4 pages), N/A, UC Berkeley.

Novak et al. "BML Analyzer: a software tool for experiments on planner lipid bilayers" Bio Techniques 42.3 (2007): pp. 335-341.

Osaki et al., "Multichannel simultaneous measurements of single-molecule translocation in alpha-hemolysin nanopore array" American Chemical Society, Nov. 12, 2009.

Polak et al. "System for measuring planar lipid bilayer properties" The Journal of membrane biology 245.10 (2012): 625-632.

Sandison et al, "Air-exposure technique for the formation of artificial lipid bilayers in microsystems", Langmuir 2007, 23 pp. 8277-8284.

Suzuki, et al. Highly reproducible method of planar lipid bilayer reconstitution in polymethyl methacrylate microfluidicchip. Langmuir. Feb. 14, 2006;22(4):1937-42.

Written opinion issued in corresponding PCT application No. PCT/E P2017/057428, 2017.

Zagnoni et al "Controlled delivery of proteins into bilayer lipid membranes on chip." Sep. 2007;7(9):1176-83.

* cited by examiner

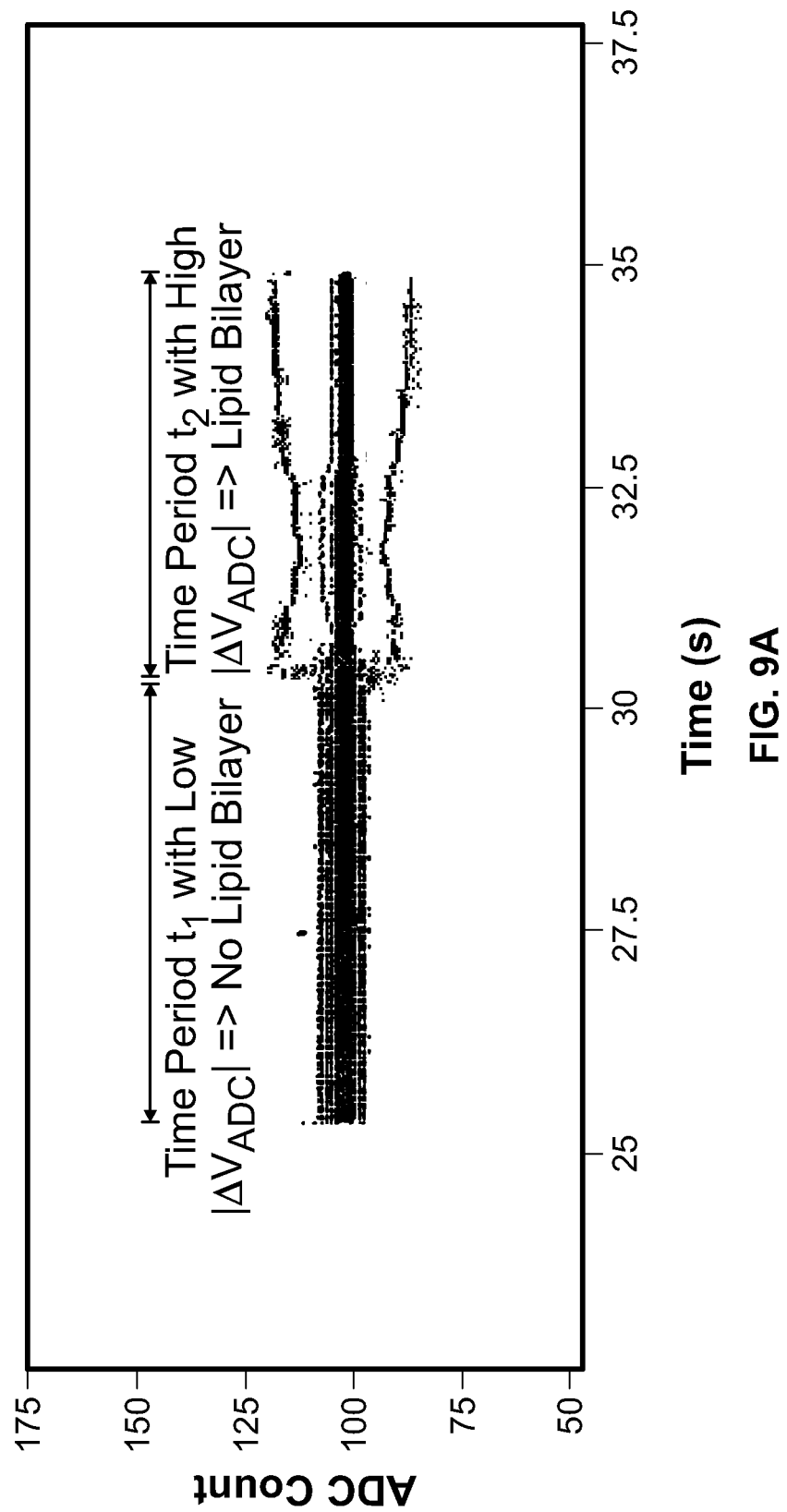

ELECTRICAL ENHANCEMENT OF BILAYER FORMATION

CROSS REFERENCE TO OTHER APPLICATIONS

This application is a continuation of U.S. patent application Ser. No. 17/304,455, filed Jun. 21, 2021, which is a continuation of U.S. patent application Ser. No. 16/578,189, filed Sep. 20, 2019, now U.S. Pat. No. 11,041,198, which is a divisional application of U.S. patent application Ser. No. 15/085,713, entitled ELECTRICAL ENHANCEMENT OF BILAYER FORMATION, filed Mar. 30, 2016, now U.S. Pat. No. 10,465,240, each of which is incorporated herein by reference in its entirety for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

FIG. 9A illustrates an exemplary plot of $V_{ADC}$ versus time before and after a lipid bilayer is formed within a cell.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
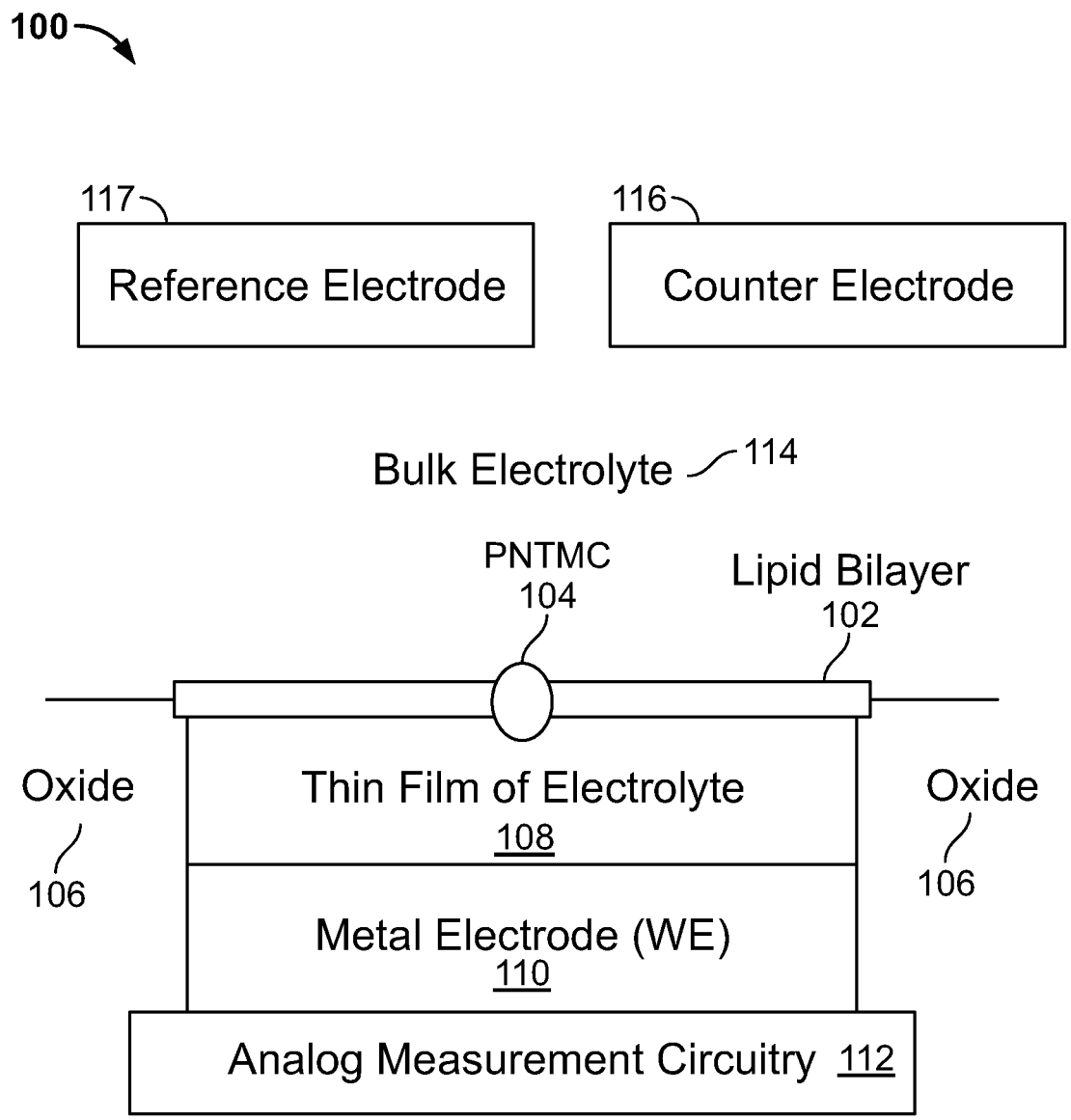
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
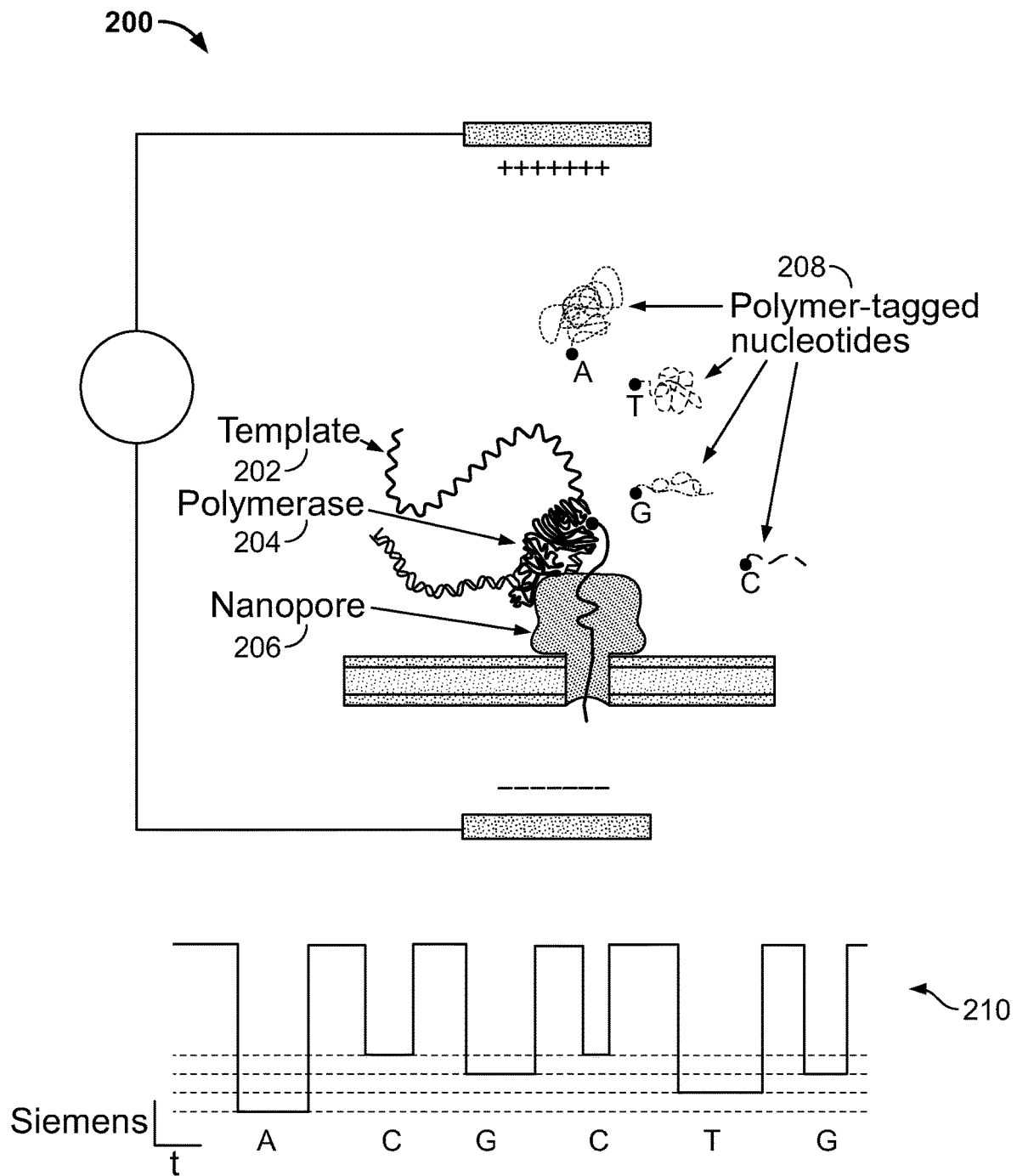
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
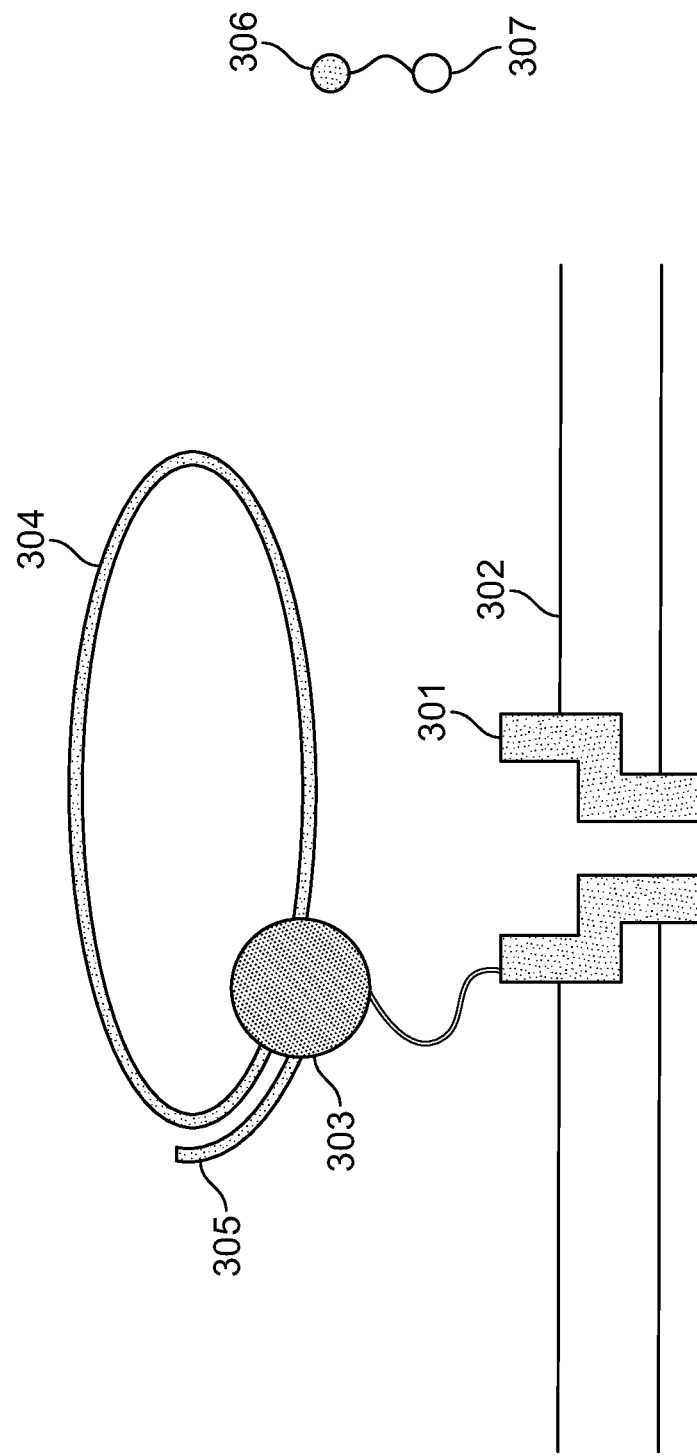
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
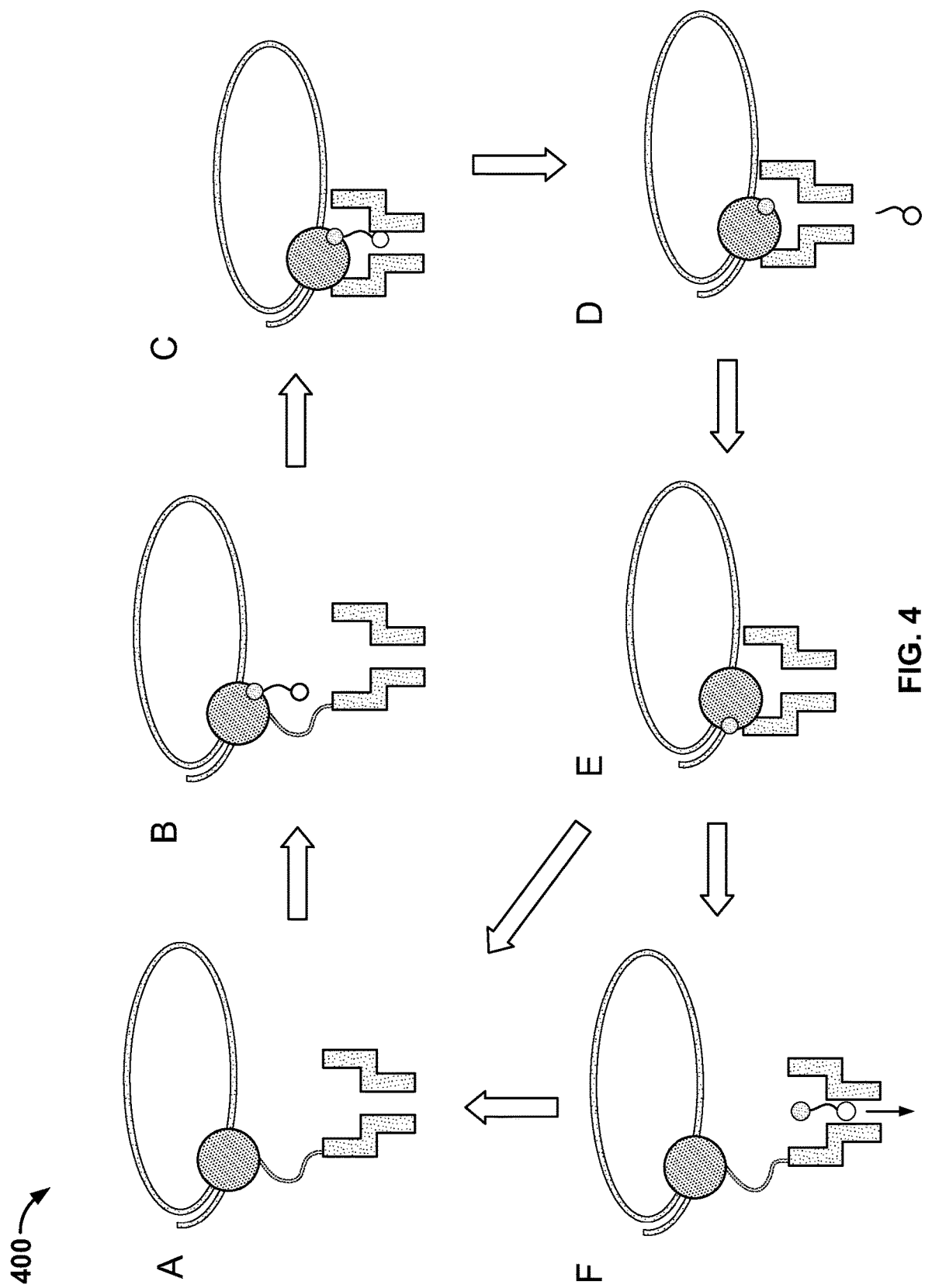
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 picosiemens (300 pS). At stage C, the conductance of the nanopore is about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
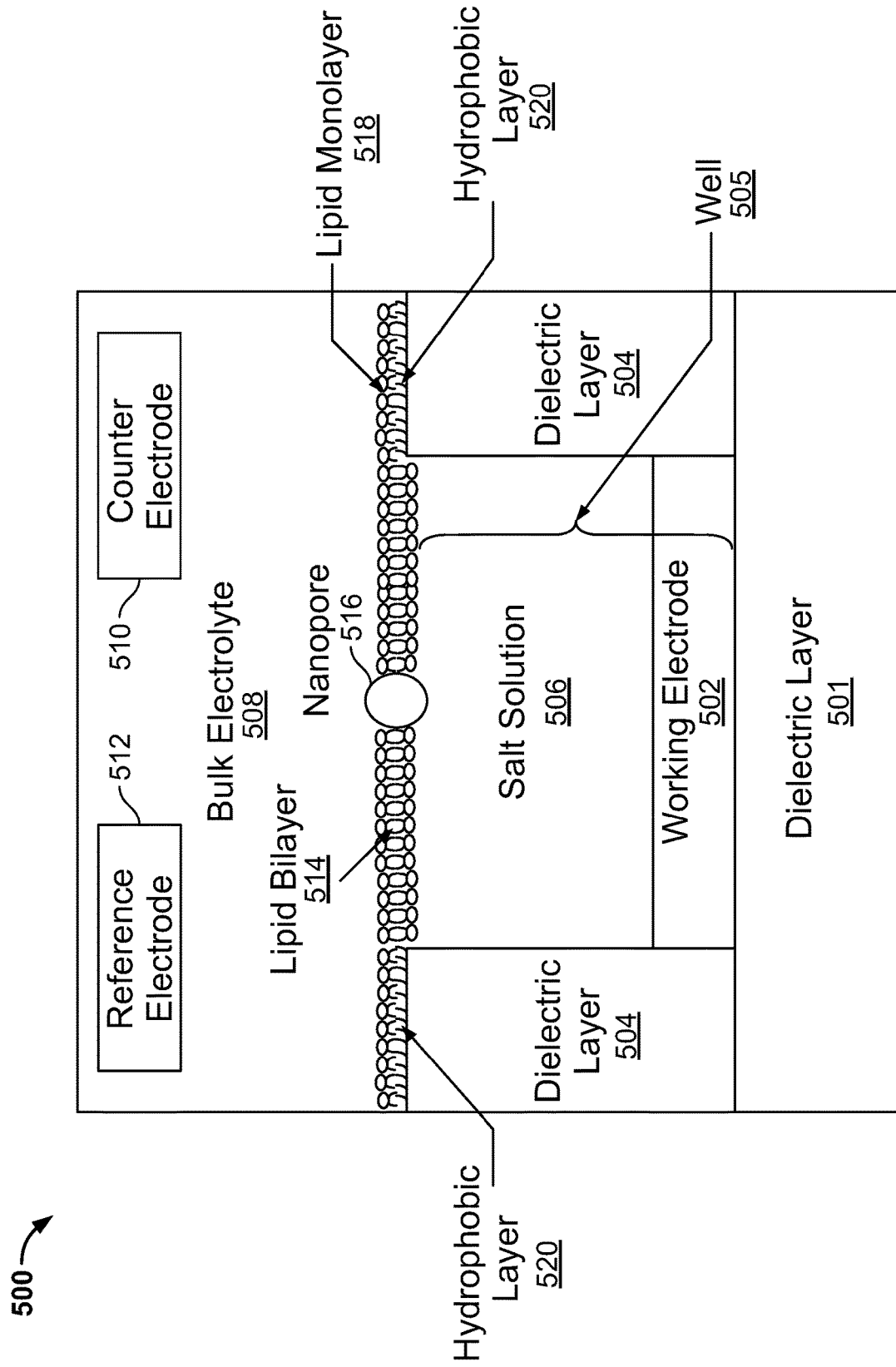
FIG. 5 illustrates an embodiment of a cell 500 in a nanopore based sequencing chip.

FIG. 5 illustrates an embodiment of a cell 500 in a nanopore based sequencing chip. Cell 500 includes a dielectric layer 501. Dielectric material used to form dielectric layer 501 includes glass, oxides, nitrides, and the like. Cell 500 further includes a dielectric layer 504 above dielectric layer 501. Dielectric layer 504 forms the walls surrounding a well 505 in which a working electrode 502 is located at the bottom. Dielectric material used to form dielectric layer 504 includes glass, oxide, silicon mononitride (SiN), and the like. The top surface of dielectric layer 504 may be silanized. Silanization forms a hydrophobic layer 520 above the top surface of dielectric layer 504. In some embodiments, hydrophobic layer 520 has a thickness of about 1.5 nanometer (nm).

Well 505 formed by the dielectric layer walls 504 further includes a film of salt solution 506 above working electrode 502. Salt solution 506 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride (CaCl$_2$), strontium chloride (SrCl$_2$), Manganese chloride (MnCl$_2$), and magnesium chloride (MgCl$_2$). In some embodiments, the film of salt solution 506 has a thickness of about three microns (μm).

As shown in FIG. 5, a membrane is formed on top of dielectric layer 504 and spans across well 505. For example, the membrane includes a lipid monolayer 518 formed on top of hydrophobic layer 520. As the membrane reaches the opening of well 505, the lipid monolayer transitions to a lipid bilayer 514 that spans across the opening of the well. A bulk electrolyte 508 containing protein nanopore transmembrane molecular complexes (PNTMC) and the analyte of interest is placed directly above the well. A single PNTMC/nanopore 516 is inserted into lipid bilayer 514 by electroporation. Nanopore 516 crosses lipid bilayer 514 and provides the only path for ionic flow from bulk electrolyte 508 to working electrode 502. Bulk electrolyte 508 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride (CaCl$_2$), strontium chloride (SrCl$_2$), Manganese chloride (MnCl$_2$), and magnesium chloride (MgCl$_2$).

Cell 500 includes a counter electrode (CE) 510, which is an electrochemical potential sensor. Cell 500 also includes a reference electrode 512. In some embodiments, counter electrode 510 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 502 is a metal electrode. For non-faradaic conduction, working electrode 502 may be made of metals that are resistant to corrosion and oxidation, e.g., platinum, gold, titanium nitride and graphite. For example, working electrode 502 may be a platinum electrode with electroplated platinum. In another example, working electrode 502 may be a titanium nitride (TiN) working electrode.

The step of inserting a nanopore into a lipid bilayer is performed after it is determined that a lipid bilayer has been properly formed within a cell of the nanopore based sequencing chip. In some techniques, the process of determining whether a lipid bilayer has been properly formed in a cell may cause an already properly formed lipid bilayer to be destroyed. For example, a stimulus voltage may be applied to cause a current to flow across the electrodes. Although the measured response to the stimulus voltage may be used to distinguish between a cell with a properly formed lipid bilayer (i.e., a lipid bilayer that is two layers of lipid molecules thick) from a cell without a properly formed lipid bilayer (e.g., a cell with a thick lipid and solvent combined film that spans across the well of the cell), the stimulus voltage level is high enough to cause an already properly formed lipid bilayer to break down in some instances. In other words, the stimulus voltage for testing the lipid bilayer may be destructive to the lipid bilayer. In the event that an already properly formed lipid bilayer is destroyed by the stimulus voltage, a very high current begins to flow across the electrodes as a result of the short-circuit condition. In response, the system may try to reform a new lipid bilayer in the particular cell again; however, this is both time-consuming and inefficient. In addition, a lipid bilayer may not reform in the particular cell in a subsequent trial. As a result, the overall percentage of cells in the nanopore based sequencing chip with properly formed lipid bilayers and nanopores (i.e., the yield of the nanopore based sequencing chip) is reduced.

A non-destructive technique to detect a lipid bilayer formed in a cell of a nanopore based sequencing chip is disclosed. A non-destructive technique to detect a lipid bilayer has many advantages, including increasing the efficiency and yield of the nanopore based sequencing chip.

Figure 6A:
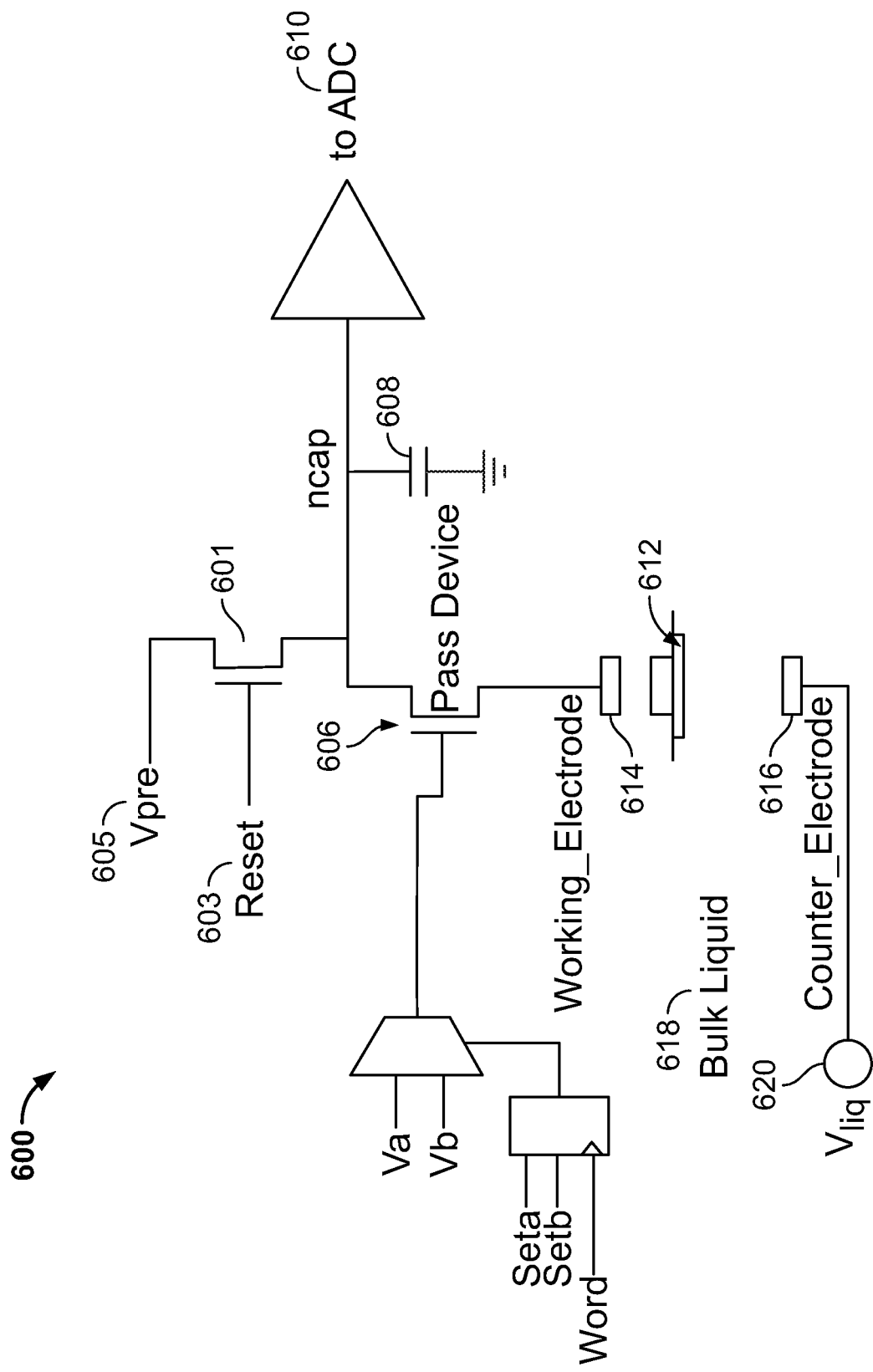
FIG. 6A illustrates an embodiment of a circuitry 600 in a cell of a nanopore based sequencing chip, wherein the circuitry can be configured to detect whether a lipid bilayer is formed in the cell without causing an already formed lipid bilayer to break down.

FIG. 6A illustrates an embodiment of a circuitry 600 in a cell of a nanopore based sequencing chip wherein the circuitry can be configured to detect whether a lipid bilayer is formed in the cell without causing an already formed lipid bilayer to break down.

FIG. 6A shows a lipid membrane or lipid bilayer 612 situated between a cell working electrode 614 and a counter electrode 616, such that a voltage is applied across lipid membrane/bilayer 612. A lipid bilayer is a thin membrane made of two layers of lipid molecules. A lipid membrane is a membrane made of several layers (more than two) of lipid molecules. Lipid membrane/bilayer 612 is also in contact with a bulk liquid/electrolyte 618. Note that working electrode 614, lipid membrane/bilayer 612, and counter electrode 616 are drawn upside down as compared to the working electrode, lipid bilayer, and counter electrode in FIG. 1. In some embodiments, the counter electrode is shared between a plurality of cells, and is therefore also referred to as a common electrode. The common electrode can be configured to apply a common potential to the bulk liquid in contact with the lipid membranes/bilayers in the measurements cells by connecting the common electrode to a voltage source $V_{liq}$ 620. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

Figure 6B:
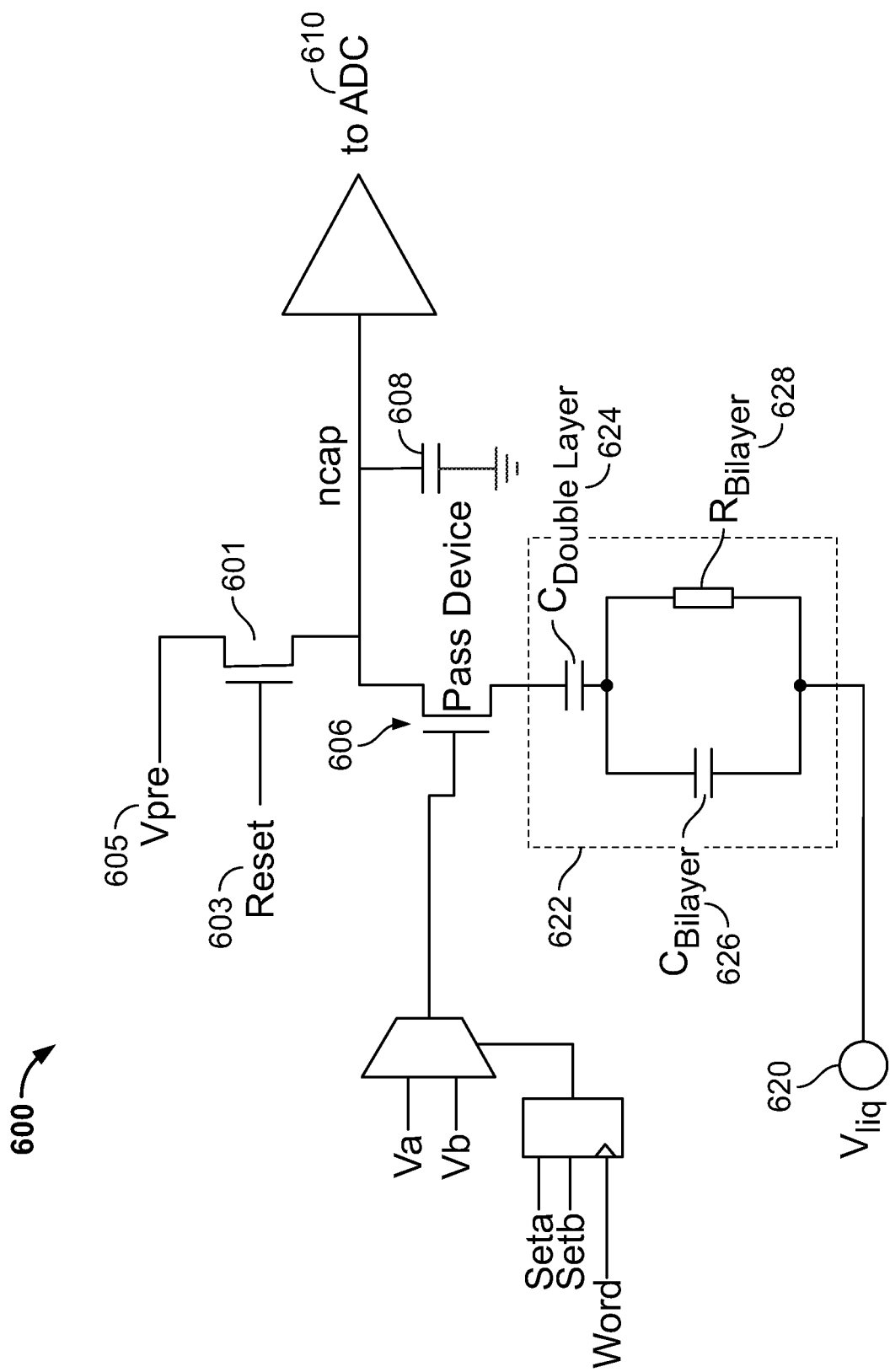
FIG. 6B illustrates the same circuitry 600 in a cell of a nanopore based sequencing chip as that shown in FIG. 6A. Comparing to FIG. 6A, instead of showing a lipid membrane/bilayer between the working electrode and the counter electrode, an electrical model representing the electrical properties of the working electrode and the lipid membrane/bilayer is shown.

FIG. 6B illustrates the same circuitry 600 in a cell of a nanopore based sequencing chip as that shown in FIG. 6A. Comparing to FIG. 6A, instead of showing a lipid membrane/bilayer between the working electrode and the counter electrode, an electrical model representing the electrical properties of the working electrode and the lipid membrane/bilayer is shown.

Electrical model 622 includes a capacitor 624 representing the electrical properties of working electrode 614. The capacitance associated with working electrode 614 is also referred to as a double layer capacitance ($C_{double\ layer}$). Electrical model 622 further includes a capacitor 626 ($C_{bilayer}$) that models a capacitance associated with the lipid membrane/bilayer and a resistor 628 ($R_{bilayer}$) that models a resistance associated with the lipid membrane/bilayer. The resistance associated with the lipid membrane/bilayer is very high, and therefore $R_{bilayer}$ may be replaced by an open circuit, which reduces electrical model 622 to $C_{double\ layer}$ in series with $C_{bilayer}$.

Voltage source $V_{liq}$ 620 is an alternating current (AC) voltage source. Counter electrode 616 is immersed in the bulk liquid 618, and an AC non-Faradaic mode is utilized to modulate a square wave voltage $V_{liq}$ and apply it to the bulk liquid in contact with the lipid membranes/bilayers in the measurement cells. In some embodiments, $V_{liq}$ is a square wave with a magnitude of ±200-250 mV and a frequency between 25 and 100 Hz.

Pass device 606 is a switch that can be used to connect or disconnect the lipid membrane/bilayer and the electrodes from the measurement circuitry 600. The switch enables or disables a voltage stimulus that can be applied across the lipid membrane/bilayer in the cell. Before lipids are deposited to the cell to form a lipid bilayer, the impedance between the two electrodes is very low because the well of the cell is not sealed, and therefore switch 606 is kept open to avoid a short-circuit condition. Switch 606 may be closed once lipid solvent has been deposited to the cell that seals the well of the cell.

Circuitry 600 further includes an on-chip fabricated integrating capacitor 608 ($n_{cap}$). Integrating capacitor 608 is pre-charged by using a reset signal 603 to close switch 601, such that integrating capacitor 608 is connected to a voltage source $V_{pre}$ 605. In some embodiments, voltage source $V_{pre}$ 605 provides a constant positive voltage with a magnitude of 900 mV. When switch 601 is closed, integrating capacitor 608 is pre-charged to the positive voltage level of voltage source $V_{pre}$ 605.

After integrating capacitor 608 is pre-charged, reset signal 603 is used to open switch 601 such that integrating capacitor 608 is disconnected from voltage source $V_{pre}$ 605. At this point, depending on the level of $V_{liq}$, the potential of counter electrode 616 may be at a higher level than the potential of working electrode 614, or vice versa. For example, during the positive phase of square wave $V_{liq}$ (i.e., the dark period of the AC voltage source signal cycle), the potential of counter electrode 616 is at a higher level than the potential of working electrode 614. Similarly, during the negative phase of square wave $V_{liq}$ (i.e., the bright period of the AC voltage source signal cycle), the potential of counter electrode 616 is at a lower level than the potential of working electrode 614. Due to this potential difference, integrating capacitor 608 may be charged during the dark period of the AC voltage source signal cycle and discharged during the bright period of the AC voltage source signal cycle.

Depending on the sampling rate of an analog-to-digital converter (ADC) 610, integrating capacitor 608 charges or discharges for a fixed period of time, and then the voltage stored in integrating capacitor 608 may be read out by ADC 610. After the sampling by ADC 610, integrating capacitor 608 is pre-charged again by using reset signal 603 to close switch 601, such that integrating capacitor 608 is connected to voltage source $V_{pre}$ 605 again. In some embodiments, the sampling rate of ADC 610 is between 1500 to 2000 Hz. In some embodiments, the sampling rate of ADC 610 is up to 5 kHz. For example, with a sampling rate of 1 kHz, integrating capacitor 608 charges or discharges for a period of ~1 ms, and then the voltage stored in integrating capacitor 608 is read out by ADC 610. After the sampling by ADC 610, integrating capacitor 608 is pre-charged again by using reset signal 603 to close switch 601 such that integrating capacitor 608 is connected to voltage source $V_{pre}$ 605 again. The steps of pre-charging the integrating capacitor 608, waiting a fixed period of time for the integrating capacitor 608 to charge or discharge, and sampling the voltage stored in integrating capacitor by ADC 610 are then repeated in cycles throughout a lipid bilayer measurement phase of the system.

Circuitry 600 may be used to detect whether a lipid bilayer is formed in the cell by monitoring a delta voltage change, $\Delta V_{ADC}$, at integrating capacitor 608 ($n_{cap}$) in response to a delta voltage change ($\Delta V_{liq}$) applied to the bulk liquid in contact with the lipid membrane/bilayer. As will be described in greater detail below, during the lipid bilayer measurement phase, circuitry 600 may be modeled as a voltage divider with $C_{bilayer}$ 626, $C_{double\ layer}$ 624, and $n_{cap}$ 608 connected in series, and a voltage change tapped at an intermediate point of the voltage divider can be read by ADC 610 for determining whether a lipid bilayer has been formed.

Figure 7:
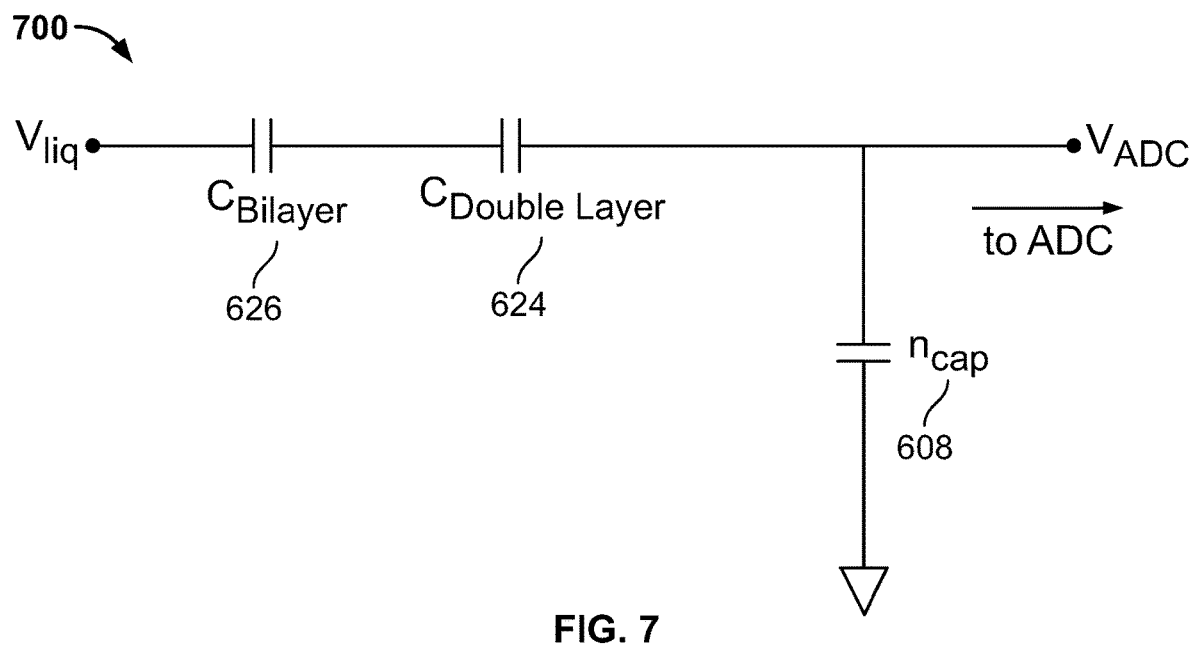
FIG. 7 illustrates an electrical model 700 representing the electrical properties of a portion of circuitry 600 during the lipid bilayer measurement phase of the system.

FIG. 7 illustrates an electrical model 700 representing the electrical properties of a portion of circuitry 600 during the lipid bilayer measurement phase of the system. As shown in FIG. 7, $C_{double\ layer}$ 624 is connected in series with $C_{bilayer}$ 626, but $R_{bilayer}$ 628 (see FIG. 6B) is eliminated from electrical model 700. $R_{bilayer}$ 628 can be removed from electrical model 700 because the resistance associated with the lipid membrane/bilayer is very high, and therefore $R_{bilayer}$ may be approximated as an open circuit. As shown in FIG. 7, $C_{double\ layer}$ 624 and $C_{bilayer}$ 626 are further connected in series with $n_{cap}$ 608.

When operating in an AC mode, the voltage read by the ADC ($V_{ADC}$) can be determined by:

$$V_{ADC} = V_{liq} * \frac{Z(ncap)}{Z(\text{bilayer}) + Z(\text{double layer}) + Z(ncap)} \quad \text{Equation (1)}$$

where $Z = 1/(j\omega C)$,

Z(ncap) is the AC impedance associated with $n_{cap}$,
Z(double layer) is the AC impedance associated with the working electrode,
and Z(bilayer) is the AC impedance associated with the lipid membrane/bilayer.

The AC impedance of the double layer, Z(double layer), has a very low value compared to Z(bilayer) and Z(ncap) because $C_{double\ layer}$ is much larger than $C_{bilayer}$ or the capacitance of $n_{cap}$. Therefore, substituting $Z(ncap)=1/(j\omega C_{ncap})$, $Z(\text{bilayer})=1/j\omega C_{bilayer}$, and Z(double layer)=0, equation (1) can be simplified as:

$$V_{ADC} = V_{liq} * \frac{C(\text{bilayer})}{C(ncap) + C(\text{bilayer})} \quad \text{Equation (2)}$$

where C(ncap) is the capacitance associated with $n_{cap}$, and C(bilayer) is the capacitance associated with the lipid membrane/bilayer.

When lipids are first deposited into the cells to form the lipid bilayers, some of the cells have lipid bilayers spontaneously formed, but some of the cells merely have a thick lipid membrane (with multiple layers of lipid molecules and solvent combined together) spanning across each of the wells of the cells. The capacitance associated with a lipid bilayer is larger than the capacitance associated with a lipid membrane that is more than two layers of lipid molecules thick because the capacitance of the lipid membrane/bilayer is inversely proportional to its thickness. As a lipid membrane thins out and transitions to become a lipid bilayer, the thickness decreases and its associated capacitance increases. In Equation (2) above, as a lipid bilayer begins to form within a cell, C(bilayer) increases while C(ncap) remains constant, such that on the whole $V_{ADC}$ increases. An increase in $V_{ADC}$ can therefore be used as an indicator that a lipid bilayer has been formed within a cell.

In some embodiments, a delta voltage change $\Delta V_{ADC}$ at integrating capacitor 608 ($n_{cap}$) in response to a delta voltage change ($\Delta V_{liq}$) applied to the bulk liquid in contact with the lipid membrane/bilayer is monitored in order to detect whether a lipid bilayer has been formed in a cell. For example, Equation (2) may be rewritten as:

$$\Delta V_{ADC} = \Delta V_{liq} * \frac{C(\text{bilayer})}{C(ncap) + C(\text{bilayer})} \quad \text{Equation (3)}$$

where $\Delta V_{ADC}$ is a voltage change at integrating capacitor 608 ($n_{cap}$) read by the ADC,
$\Delta V_{liq}$ is a voltage change applied to the bulk liquid,
C(ncap) is the capacitance associated with $n_{cap}$,
and C(bilayer) is the capacitance associated with the lipid membrane/bilayer.

In Equation (3) above, because C(ncap) remains constant, while C(bilayer) increases as a lipid bilayer begins to form within a cell, $\Delta V_{ADC}$ increases as well. $\Delta V_{ADC}$ is roughly proportional to the capacitance associated with the lipid membrane/bilayer, C(bilayer). An increase in $\Delta V_{ADC}$ can therefore be used as an indicator that a lipid bilayer has been formed within a cell.

In some embodiments, in order to maximize the observable $\Delta V_{ADC}$ for a more reliable detection of a lipid bilayer, $\Delta V_{ADC}$ in response to a maximum voltage change applied to the bulk liquid in contact with the lipid membrane/bilayer (max $\Delta V_{liq}$) is monitored in order to detect whether a lipid bilayer has been formed in a cell.

Figure 8A:
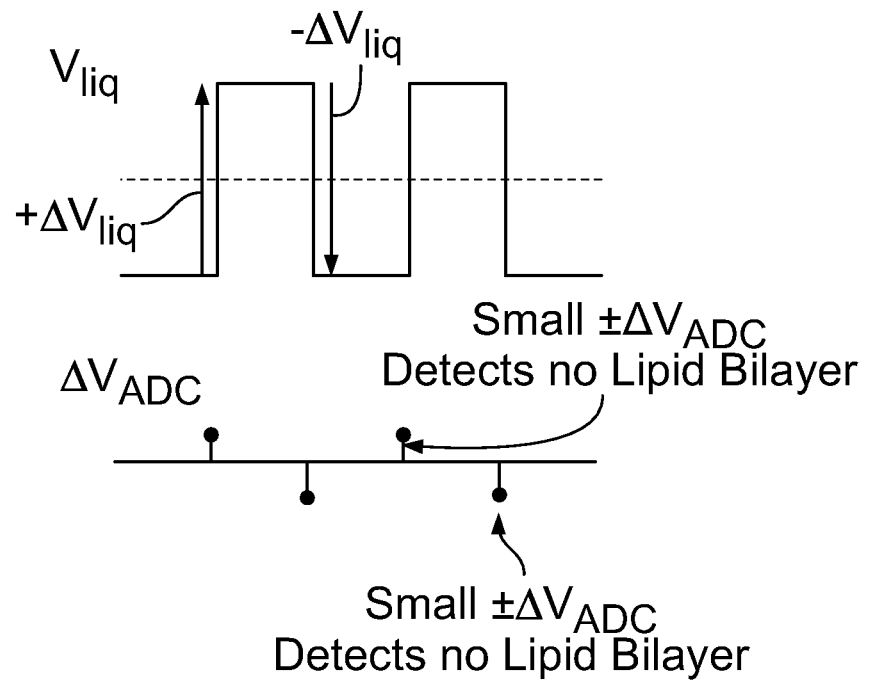
FIG. 8A illustrates that a small observed $\pm\Delta V_{ADC}$ in response to a $\pm\Delta V_{liq}$ detects that no lipid bilayer has been formed in the cell.
Figure 8B:
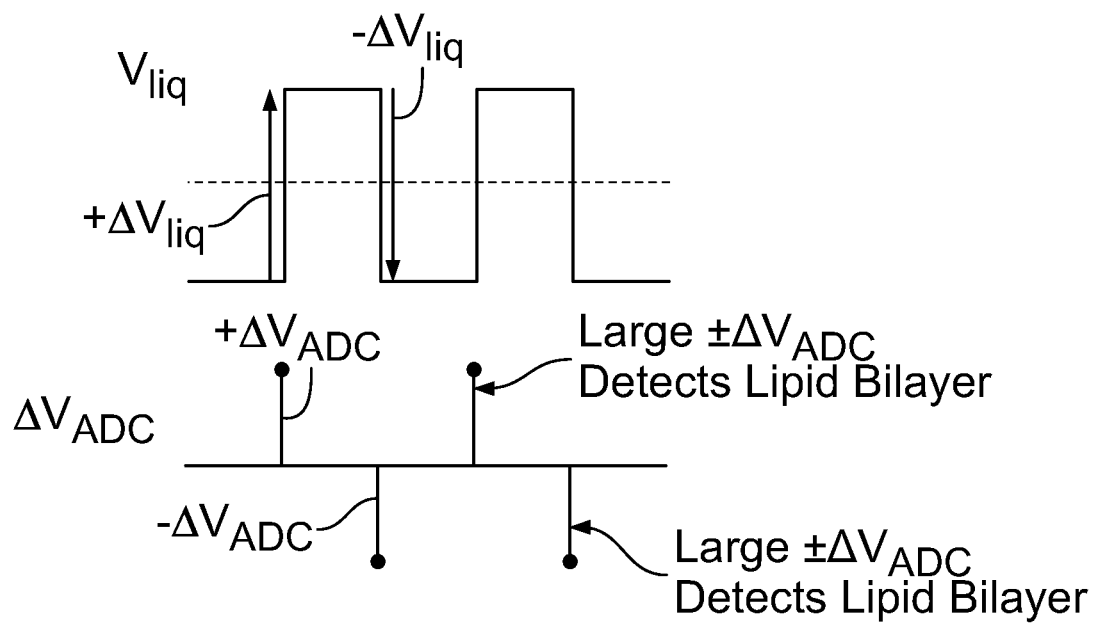
FIG. 8B illustrates that a large observed $\pm\Delta V_{ADC}$ in response to a $\pm\Delta V_{liq}$ detects that a lipid bilayer has been formed in a cell.

FIG. 8A illustrates that a small observed positive/negative voltage change $\pm\Delta V_{ADC}$ in response to a positive/negative voltage change $\pm\Delta V_{liq}$ results in no lipid bilayer being detected to have been formed in the cell. FIG. 8B illustrates that a large observed positive/negative voltage change $\pm\Delta V_{ADC}$ in response to a positive/negative voltage change $\pm\Delta V_{liq}$ results in the detection of a lipid bilayer having been formed in a cell.

In FIG. 8A, a maximum positive voltage change $+\Delta V_{liq}$ occurs when the square wave $V_{liq}$ changes from a negative phase to a positive phase, while a maximum negative voltage change $-\Delta V_{liq}$ occurs when the square wave $V_{liq}$ changes from a positive phase to a negative phase. In FIG. 8A, at the instance when $\Delta V_{liq}$ is at a positive maximum, only a small $+\Delta V_{ADC}$ can be observed if a lipid bilayer has not been formed in the cell; at the instance when $\Delta V_{liq}$ is at a negative maximum, only a small $-\Delta V_{ADC}$ can be observed if a lipid bilayer has not been formed in the cell.

In FIG. 8B, at the instance when $\Delta V_{liq}$ is at a positive maximum, a large positive voltage change $+\Delta V_{ADC}$ can be observed if a lipid bilayer has already been formed in the cell. And at the instance when $\Delta V_{liq}$ is at a negative maximum, a large negative voltage change $-\Delta V_{ADC}$ can be observed if a lipid bilayer has already been formed in the cell.

In some embodiments, the absolute value of $\Delta V_{ADC}$ ($|\Delta V_{ADC}|$) observed when the absolute value of $\Delta V_{liq}$ ($|\Delta V_{liq}|$) is at a maximum is compared with a predetermined threshold. If ($|\Delta V_{ADC}|$>predetermined threshold), then it is determined that a lipid bilayer is detected. Conversely, if ($|\Delta V_{ADC}|$<predetermined threshold), then it is determined that a lipid bilayer is not detected.

FIG. 9A illustrates an exemplary plot of $V_{ADC}$ versus time before and after a lipid bilayer is formed within a cell. The plot in FIG. 9A is based on real testing data. As shown in FIG. 9A, the units of $V_{ADC}$ on the y-axis are in ADC counts. However, other units may be used as well. As shown in FIG. 9A, during a time period $t_1$ when a lipid bilayer has not been formed, the recorded $|\Delta V_{ADC}|$ values are smaller than those recorded during a time period $t_2$ after a lipid bilayer has been formed in the cell.

Figure 9B:
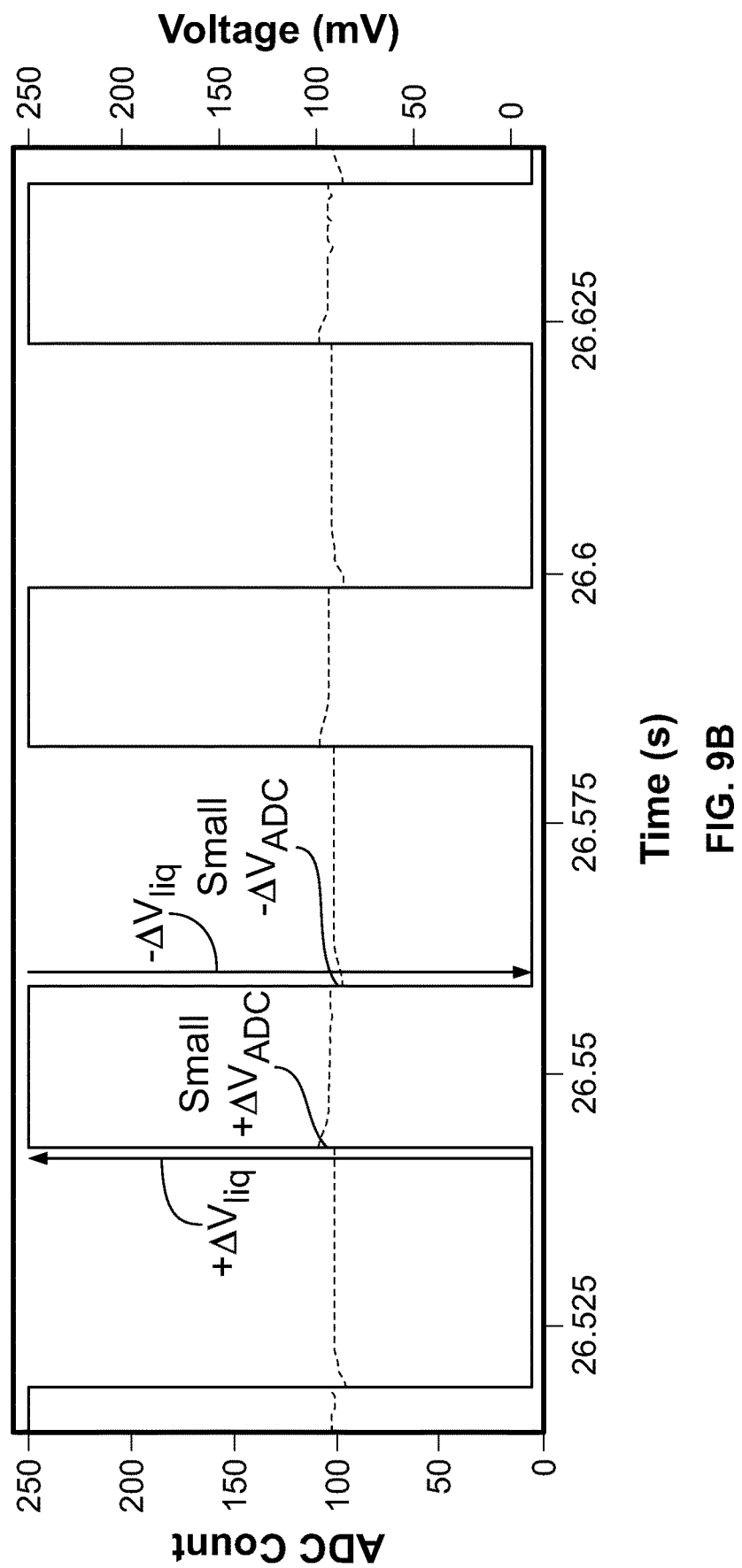
FIG. 9B illustrates a zoomed-in view of the exemplary plot of $V_{ADC}$ versus time (see FIG. 9A) during the time period $t_1$ when a lipid bilayer has not been formed.

FIG. 9B illustrates a zoomed-in view of the exemplary plot of $V_{ADC}$ versus time (see FIG. 9A) during the time period $t_1$ when a lipid bilayer has not been formed. The results shown in FIG. 9B are consistent with FIG. 8A. In FIG. 9B, a maximum $+\Delta V_{liq}$ occurs when the square wave $V_{liq}$ changes from a negative phase to a positive phase, while a maximum $-\Delta V_{liq}$ occurs when the square wave $V_{liq}$ changes from a positive phase to a negative phase. In FIG. 9B, at the instance when $\Delta V_{liq}$ is at a positive maximum, only a small $+\Delta V_{ADC}$ can be observed because a lipid bilayer has not been formed in the cell; at the instance when $\Delta V_{liq}$ is at a negative maximum, only a small $-\Delta V_{ADC}$ can be observed because a lipid bilayer has not been formed in the cell.

Figure 9C:
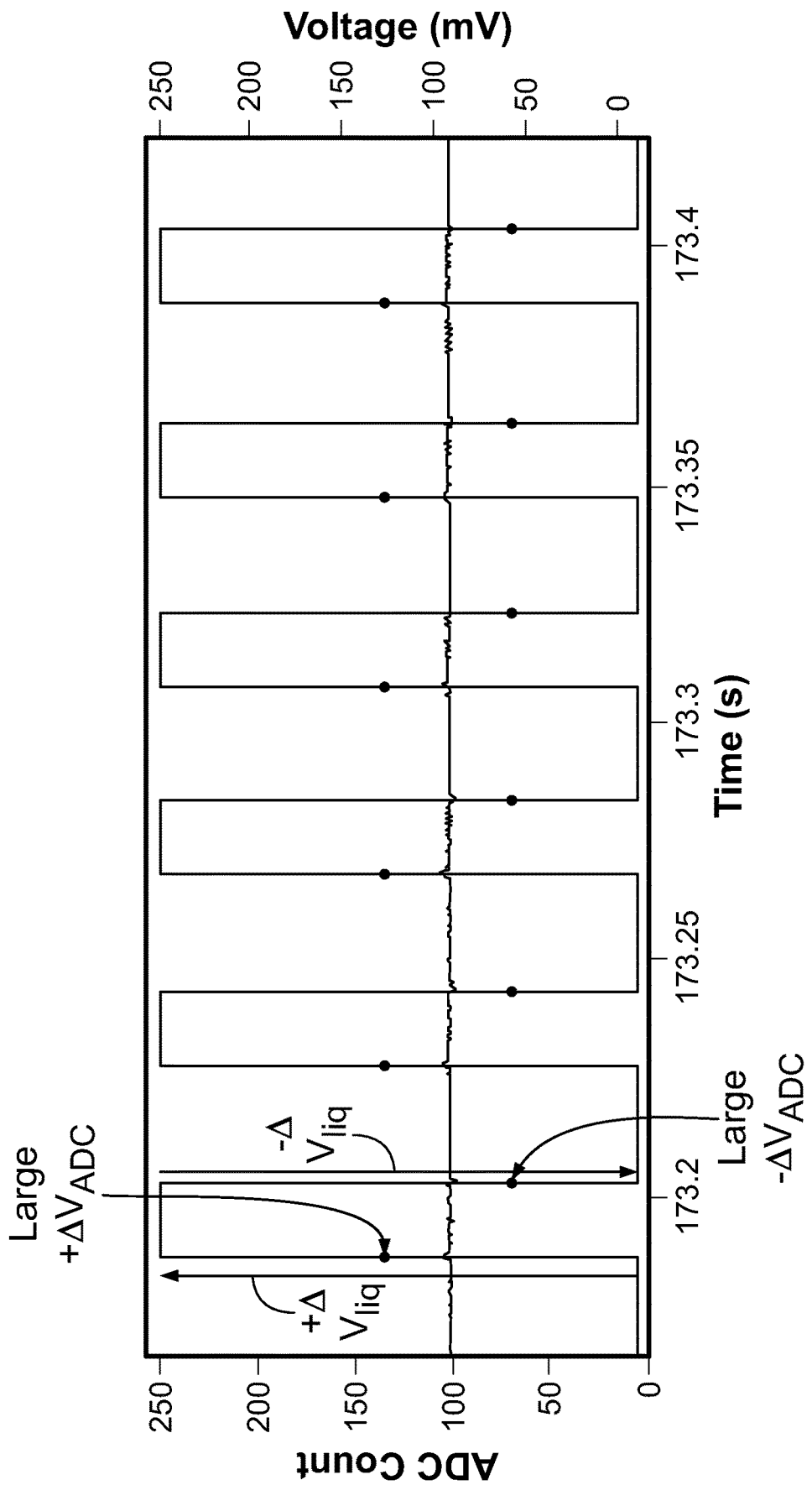
FIG. 9C illustrates a zoomed-in view of the exemplary plot of $V_{ADC}$ versus time (see FIG. 9A) during the time period $t_2$ when a lipid bilayer has been formed.

FIG. 9C illustrates a zoomed-in view of the exemplary plot of $V_{ADC}$ versus time (see FIG. 9A) during the time period $t_2$ when a lipid bilayer has been formed. The results shown in FIG. 9C are consistent with FIG. 8B. In FIG. 9C, at the instance when $\Delta V_{liq}$ is at a positive maximum, a large $+\Delta V_{ADC}$ can be observed between two consecutive sample points because a lipid bilayer has already been formed in the cell. At the instance when $\Delta V_{liq}$ is at a negative maximum, a large $-\Delta V_{ADC}$ can be observed because a lipid bilayer has already been formed in the cell. Note that shortly after the square wave $V_{liq}$ changes from one phase to another, $\Delta V_{liq}$ stays at zero, and $V_{ADC}$ reduces to zero in response. As shown in FIG. 9C, when a lipid bilayer has already been formed in the cell, a positive or negative spike in $V_{ADC}$ can be observed. The positive or negative spikes are followed by much smaller $V_{ADC}$ values.

As described above, when the lipid solvent mixture is first deposited into the cells to form the lipid bilayers, some of the cells have lipid bilayers spontaneously formed, but some of the cells merely have a thick lipid membrane with multiple layers of lipid molecules combined with the solvent spanning across each of the wells of the cells. In order to increase the yield of the nanopore based sequencing chip (i.e., the percentage of cells in the nanopore based sequencing chip with properly formed lipid bilayers and nanopores), the nanopore based sequencing chip may perform additional steps to facilitate the formation of lipid bilayers in additional cells. For example, applying an electrical lipid-thinning stimulus to the cells that have not had lipid bilayers formed therein yet can improve the efficiency of liquid flow above the thick lipid membranes, thereby facilitating the removal of any excess lipid solvent such that the thick lipid membranes can be thinned out and transitioned into lipid bilayers more efficiently. Applying the electrical lipid-thinning stimulus to the cells that have not had lipid bilayers formed therein yet will also create electrostatic forces that tend to squeeze out the excess lipid solvent and thin out the thick lipid membranes into lipid bilayers. On the other hand, the cells that have already had lipid bilayers properly formed therein should not be further exposed to the same electrical lipid-thinning stimulus, as the electrical stimulus may cause some of the thin lipid bilayers to break down. Therefore, it is advantageous to use the non-destructive technique described in the present application to detect and separate the portion of the cells in the nanopore based sequencing chip that have lipid bilayers formed therein from the portion of the cells that do not have lipid bilayer properly formed therein yet. By dividing the cells into different groups, the cells in different groups can be processed differently, thereby achieving greater efficiency and increasing the overall yield of the nanopore based sequencing chip.

Figure 10:
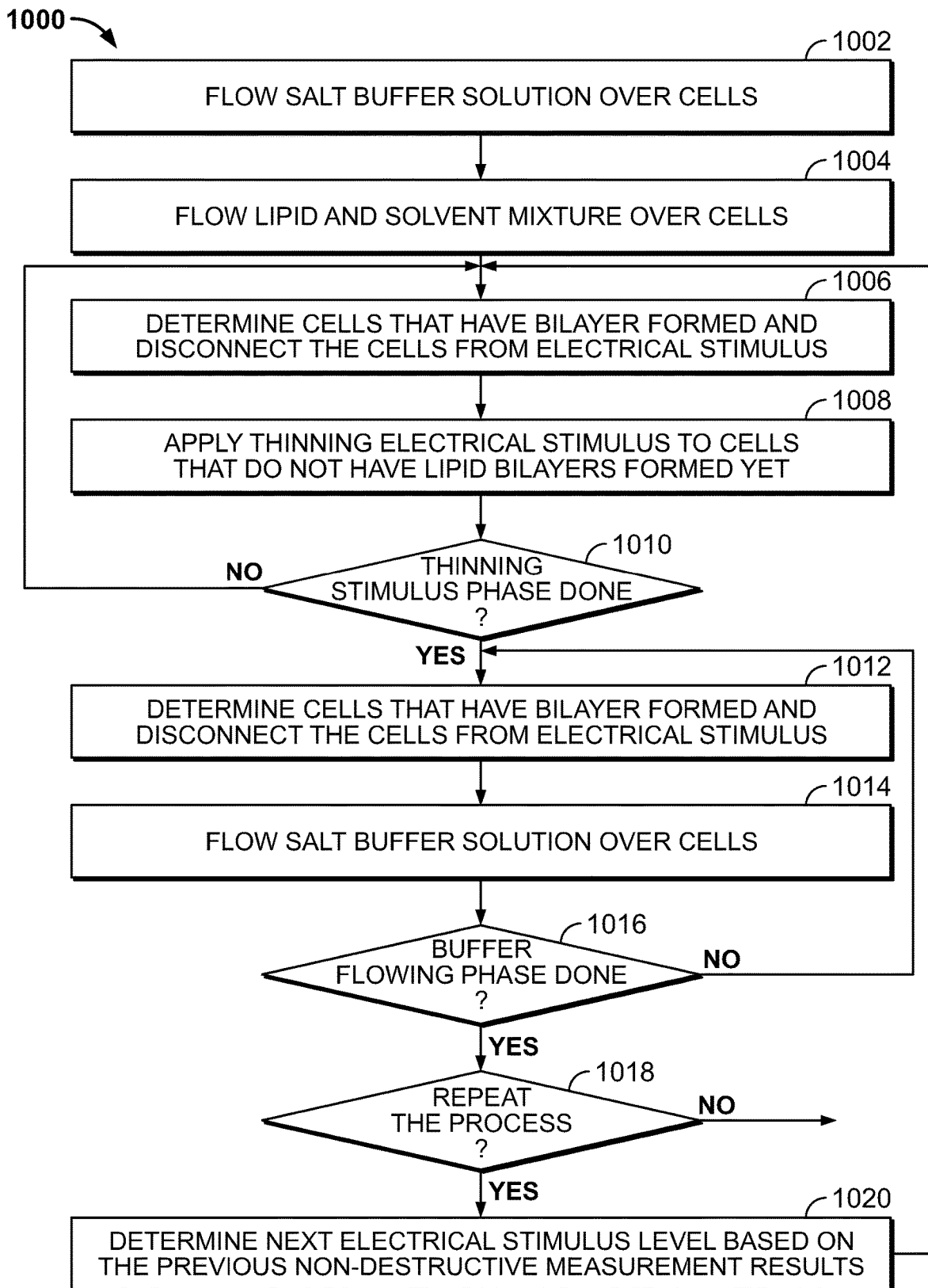
FIG. 10 illustrates an embodiment of a process 1000 for an improved technique of forming lipid layers in the cells of a nanopore based sequencing chip.

FIG. 10 illustrates an embodiment of a process 1000 for an improved technique of forming lipid layers in the cells of a nanopore based sequencing chip. In some embodiments, the nanopore based sequencing chip of FIG. 10 includes a plurality of cells 100 of FIG. 1. In some embodiments, the nanopore based sequencing chip of FIG. 10 includes a plurality of cells 500 of FIG. 5. In some embodiments, the nanopore based sequencing chip of FIG. 10 includes circuitries 600 of FIGS. 6A and 6B.

Process 1000 includes steps in which different types of fluids (e.g., liquids or gases) are flowed through the cells of the nanopore based sequencing chip via a flow chamber. Multiple fluids with significantly different properties (e.g., compressibility, hydrophobicity, and viscosity) are flowed over an array of sensors on the surface of the nanopore based sequencing chip. For improved efficiency, each of the sensors in the array should be exposed to the fluids in a consistent manner. For example, each of the different types of fluids should be flowed over the nanopore based sequencing chip such that the fluid may be delivered to the chip, evenly coating and contacting each of the cells' surfaces, and then delivered out of the chip. As described above, a nanopore based sequencing chip incorporates a large number of sensor cells configured as an array. As the nanopore based sequencing chip is scaled to include more and more cells, achieving an even flow of the different types of fluids across the cells of the chip becomes more challenging.

Figure 11:
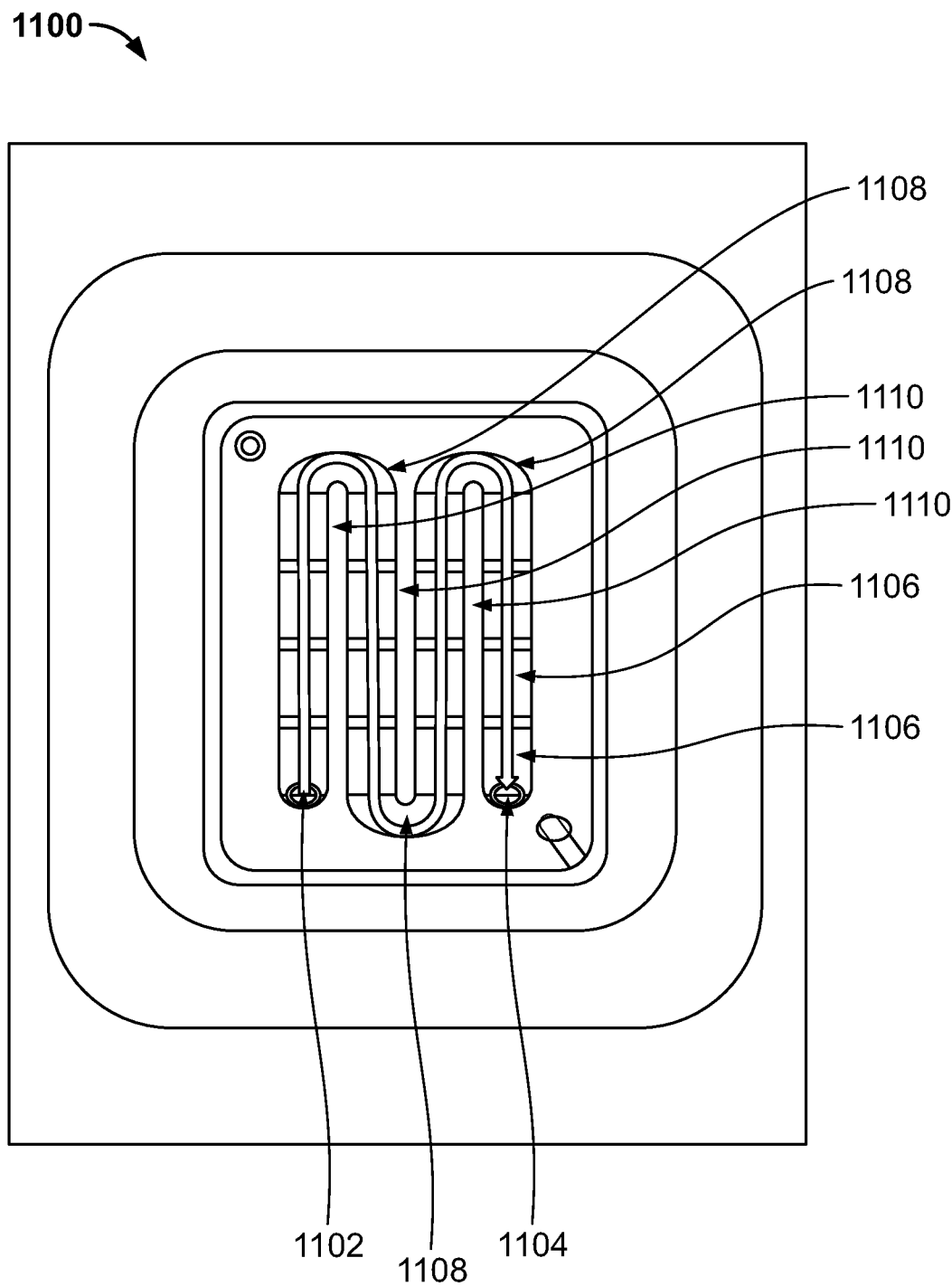
FIG. 11 illustrates the top view of a nanopore based sequencing system 1100 with an improved flow chamber enclosing a silicon chip that allows liquids and gases to pass over and contact sensors on the chip surface.

In some embodiments, the nanopore based sequencing system that performs process 1000 of FIG. 10 includes an improved flow chamber having a serpentine fluid flow channel that directs the fluids to traverse over different sensors of the chip along the length of the channel. FIG. 11 illustrates the top view of a nanopore based sequencing system 1100 with an improved flow chamber enclosing a silicon chip that allows liquids and gases to pass over and contact sensors on the chip surface. The flow chamber includes a serpentine or winding flow channel 1108 that directs the fluids to flow directly above a single column (or a single row) of sensor banks 1106 (each bank including several thousands of sensor cells) from one end of the chip to the opposite end and then directs the fluids to repeatedly loop back and flow directly above other adjacent columns of sensor banks, until all of the sensor banks have been traversed at least once. As shown in FIG. 11, system 1100 includes an inlet 1102 and an outlet 1104.

With reference to FIG. 11, a fluid is directed into system 1100 through inlet 1102. Inlet 1102 may be a tube or a needle. For example, the tube or needle may have a diameter of one millimeter. Instead of feeding the liquid or gas directly into a wide flow chamber with a single continuous space, inlet 1102 feeds the liquid or gas into a serpentine flow channel 1108 that directs the liquid or gas to flow directly above a single column of sensor banks 1106. The serpentine channel 1108 may be formed by stacking together a top plate and a gasket with dividers 1110 that divide the chamber into the serpentine channel to form a flow cell, and then mounting the flow cell on top of the chip. Once the liquid or gas flows through the serpentine channel 1108, the liquid or gas is directed up through outlet 1104 and out of system 1100.

System 1100 allows the fluids to flow more evenly on top of all the sensors on the chip surface. The channel width is configured to be narrow enough such that capillary action has an effect. More particularly, the surface tension (which is caused by cohesion within the fluid) and adhesive forces between the fluid and the enclosing surfaces act to hold the fluid together, thereby preventing the fluid or the air bubbles from breaking up and creating dead zones. For example, the channel may have a width of 1 millimeter or less. The narrow channel enables controlled flow of the fluids and minimizes the amount of remnants from a previous flow of fluids or gases.

With reference to FIG. 10, at 1002, a salt/electrolyte buffer solution is flowed through the cells of the nanopore based sequencing chip via the flow chamber to substantially fill the wells in the cells with the salt buffer solution. The salt buffer solution may include one of the following: lithium chloride (LiCl), sodelectium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$). In some embodiments, the concentration of the salt buffer solution is 300 mM (millimolar).

At 1004, a lipid and solvent mixture is flowed through the cells of the nanopore based sequencing chip via the flow chamber. In some embodiments, the lipid and solvent mixture includes lipid molecules such as diphytanoylphosphatidylcholine (DPhPC). In some embodiments, the lipid and solvent mixture includes decane or tridecane. When the lipid and solvent mixture is first deposited into the cells to form the lipid bilayers, some of the cells have lipid bilayers spontaneously formed, but some of the cells merely have a thick lipid membrane (with multiple layers of lipid molecules and solvent combined together) spanning across each of the wells of the cells. In order to increase the yield of the nanopore based sequencing chip (i.e., the percentage of cells in the nanopore based sequencing chip with properly formed lipid bilayers and nanopores), the nanopore based sequencing chip will repeatedly go through two phases, an electrical lipid-thinning stimulus phase and a buffer flowing phase, to facilitate the formation of lipid bilayers in additional cells.

The electrical lipid-thinning stimulus phase of process 1000 includes steps 1006, 1008, and 1010. In some embodiments, during this phase steps 1006, 1008, and 1010 may be performed in the order as shown in FIG. 10. In some embodiments, steps 1006, 1008, and 1010 may be performed in a different order. In some embodiments, the steps may be performed simultaneously.

At 1006, the non-destructive technique described in the present application is used to detect whether a lipid bilayer is formed in a cell using circuitry 600 of FIG. 6A and FIG. 6B. The detection includes monitoring a voltage change, $\Delta V_{ADC}$, at integrating capacitor 608 ($n_{cap}$) in response to a voltage change ($\Delta V_{liq}$) applied to the bulk liquid in contact with the lipid membrane/bilayer. Cells that have lipid bilayers detected are separated into a different group from the cells that do not have lipid bilayers detected. Within each of the cells with lipid bilayers detected, pass device 606 is opened in order to disconnect the lipid bilayer and the electrodes from the measurement circuitry 600, such that the electrical lipid-thinning stimulus is disabled from being applied to the cell.

At 1008, an electrical lipid-thinning stimulus is applied to the cells of the nanopore based sequencing chip. Applying the electrical lipid-thinning stimulus to the cells that have not had lipid bilayers formed therein yet can improve the efficiency of liquid flow above the thick lipid membranes, thereby facilitating the removal of any excess lipid solvent such that the thick lipid membranes can be thinned out and transitioned into lipid bilayers more efficiently. Applying the electrical lipid-thinning stimulus to the cells that have not had lipid bilayers formed therein yet will also create electrostatic forces that tend to squeeze out the excess lipid solvent and thin out the thick lipid membranes into lipid bilayers. In some embodiments, the same circuitry 600 of FIG. 6A and FIG. 6B may be used to apply the electrical lipid-thinning stimulus. The only difference in the setup of circuitry 600 between lipid bilayer detection and lipid thinning is that the absolute magnitude of $V_{liq}$ is lower for lipid bilayer detection. For example, the absolute magnitude $V_{liq}$ for lipid bilayer detection may be between 100 mV to 250 mV, while the absolute magnitude $V_{liq}$ for lipid thinning may be between 250 mV to 500 mV.

At step 1010, it is determined whether the electrical lipid-thinning stimulus phase is finished. In some embodiments, the electrical lipid-thinning stimulus is applied to any cells that have not been detected as having lipid bilayers therein for a period of two seconds. However, other predetermined period of time may be used as well. If the phase is not over yet, then process 1000 returns to steps 1006 and 1008 again until the time period is finished; otherwise, process 1000 proceeds to the salt buffer solution flowing phase next.

The salt buffer solution flowing phase of process 1000 includes steps 1012, 1014, and 1016. In some embodiments, during this phase steps 1012, 1014, and 1016 may be performed in the order as shown in FIG. 10. In some embodiments, steps 1012, 1014, and 1016 may be performed in a different order. In some embodiments, the steps may be performed simultaneously.

At 1012, the same non-destructive technique used at step 1006 is used to detect whether a lipid bilayer is formed in the cell using circuitry 600 of FIG. 6A and FIG. 6B. Cells that have lipid bilayers detected are separated into a different group from the cells that do not have lipid bilayers detected. Within each of the cells with lipid bilayers detected, pass device 606 is opened in order to disconnect the lipid bilayer and the electrodes from the measurement circuitry 600.

At 1014, a salt/electrolyte buffer solution is flowed through the cells of the nanopore based sequencing chip via the flow chamber. The purpose of flowing the salt buffer solution over the cells is to facilitate the formation of a lipid bilayer over each of the cells. When the salt buffer solution is flowed over the cells, the thickness of the lipid and solvent mixture deposited on the cell is reduced, facilitating the formation of the lipid bilayer.

At 1016, it is determined whether the salt buffer solution flowing phase is over. In some embodiments, salt buffer solution is flowed for a period of two seconds. However, other predetermined period of time may be used as well. If the phase is not over yet, then process 1000 returns to steps 1012 and 1014 again until the time period is finished; otherwise, process 1000 proceeds to step 1018.

At 1018, it is determined whether the electrical lipid-thinning stimulus phase and salt buffer solution flowing phase of process 1000 should be repeated. Different criteria may be used at this step. In some embodiments, the electrical lipid-thinning stimulus phase and salt buffer solution flowing phase are performed a predetermined number of times. In some embodiments, the two phases are repeated until a target yield for the nanopore based sequencing chip has been reached. In some embodiments, if the incremental number or percentage of cells that have just been detected as having lipid bilayers formed during the last round of thinning by the stimulus and the buffer solution flow is lower than a predetermined threshold, then process 1000 is terminated. In some embodiments, the two phases are repeated until the most recently applied electrical lipid-thinning stimulus level has reached a predetermined maximum threshold, e.g. 500 mV.

Process 1000 proceeds to step 1020 if the electrical lipid-thinning stimulus phase and salt buffer solution flowing phase of process 1000 are going to be repeated next. At step 1020, the next electrical lipid-thinning stimulus to be applied is determined. In some embodiments, the electrical lipid-thinning stimulus level is increased by a fixed predetermined amount, e.g., an increment of 100 mV. In some embodiments, if the incremental number or percentage of cells that have just been detected as having lipid bilayers formed during the last iteration is lower than a predetermined threshold, then the electrical lipid-thinning stimulus level is increased by a fixed predetermined amount; otherwise, the previous electrical lipid-thinning stimulus is found to be effective and thus the same electrical lipid-thinning stimulus level is used again.

Figure 12A:
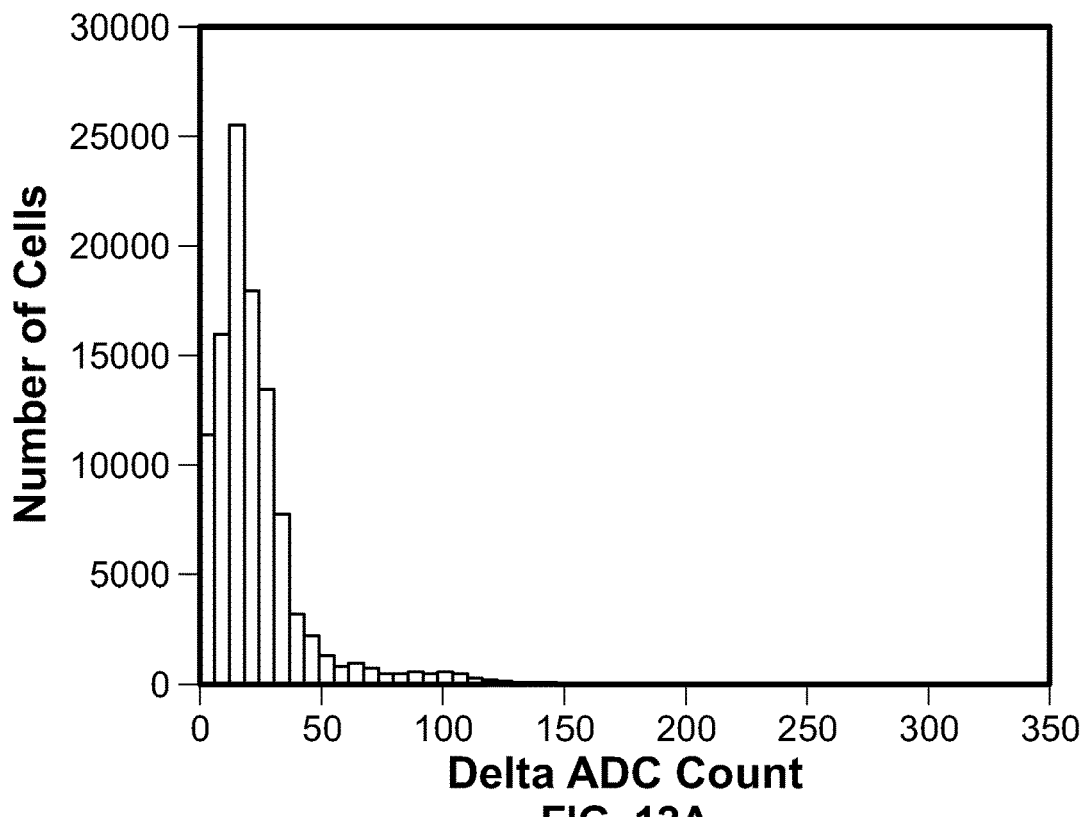
FIG. 12A illustrates the initial distribution of cells with different $\Delta V_{ADC}$ values.
Figure 12B:
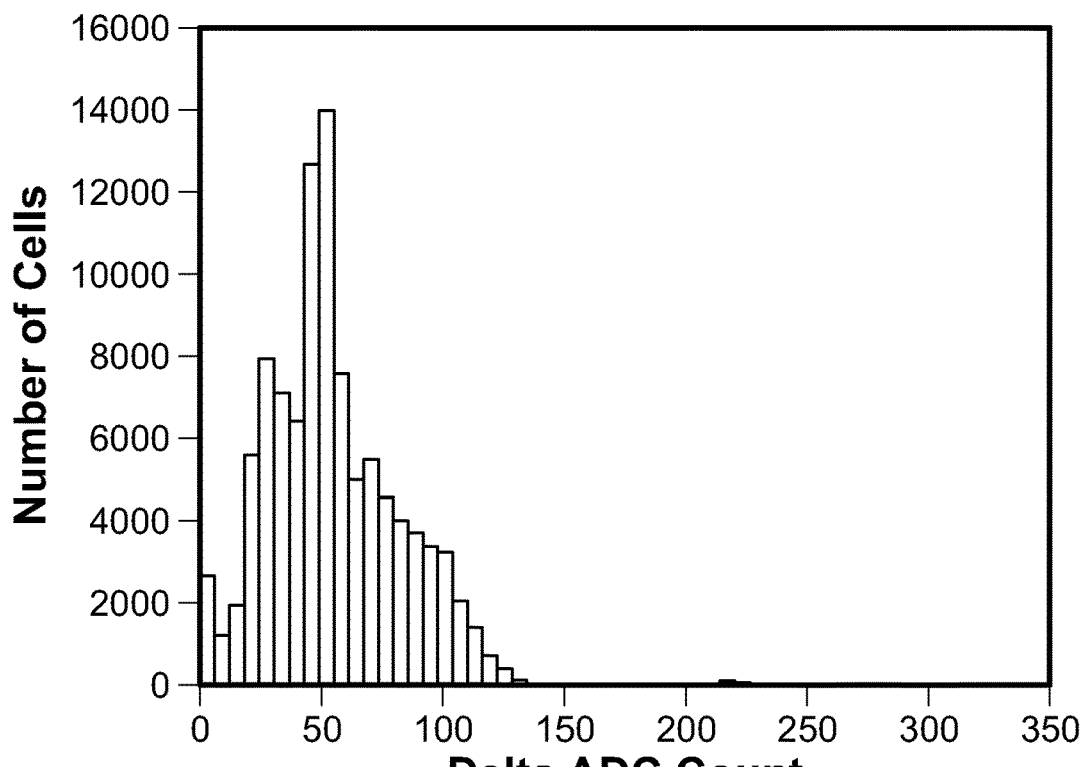
FIG. 12B illustrates the distribution of cells with different $\Delta V_{ADC}$ values after the lipid-thinning stimulus phase and salt buffer solution flowing phase of process 1000 have repeated a number of times.
Figure 12C:
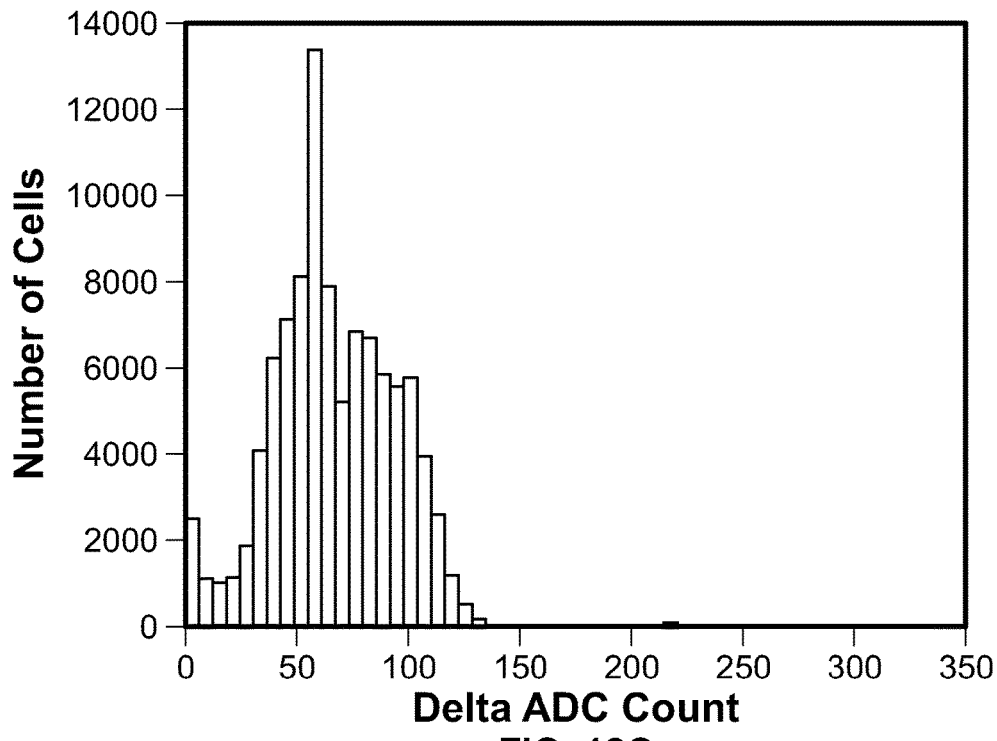
FIG. 12C illustrates the distribution of cells with different $\Delta V_{ADC}$ values after the lipid-thinning stimulus phase and salt buffer solution flowing phase of process 1000 have repeated an even greater number of times.

FIGS. 12A, 12B, and 12C are histograms that illustrate that as the electrical lipid-thinning stimulus phase and salt buffer solution flowing phase of process 1000 repeats a number of times, the overall percentage of cells in the nanopore based sequencing chip with properly formed lipid bilayers (i.e., the yield of the nanopore based sequencing chip) increases. For each of the figures, the x-axis is the voltage change at integrating capacitor 608 ($n_{cap}$), $\Delta V_{ADC}$, in response to a voltage change ($\Delta V_{liq}$) applied to the bulk liquid in contact with the lipid membrane/bilayer, while the y-axis is the number of cells with its $\Delta V_{ADC}$ value within certain $\Delta V_{ADC}$ bins. FIG. 12A illustrates the initial distribution of cells with different $\Delta V_{ADC}$ values. FIG. 12B illustrates the distribution of cells with different $\Delta V_{ADC}$ values after the lipid-thinning stimulus phase and salt buffer solution flowing phase of process 1000 have repeated a number of times. FIG. 12C illustrates the distribution of cells with different $\Delta V_{ADC}$ values after the lipid-thinning stimulus phase and salt buffer solution flowing phase of process 1000 have repeated an even greater number of times. In this example, cells that have a $\Delta V_{ADC}$ value of 50 or above are determined as having lipid bilayers formed therein. As shown in FIG. 12A, initially, only a small number of cells have lipid bilayers detected. As shown in FIG. 12B, after the lipid-thinning stimulus phase and salt buffer solution flowing phase of process 1000 have repeated a number of times, the number of cells having lipid bilayers detected increases. Finally, as shown in FIG. 12C, after the lipid-thinning stimulus phase and salt buffer solution flowing phase of process 1000 have repeated an even greater number of times, a high majority of the cells in the nanopore based sequencing chip has lipid bilayers detected.

Figure 13:
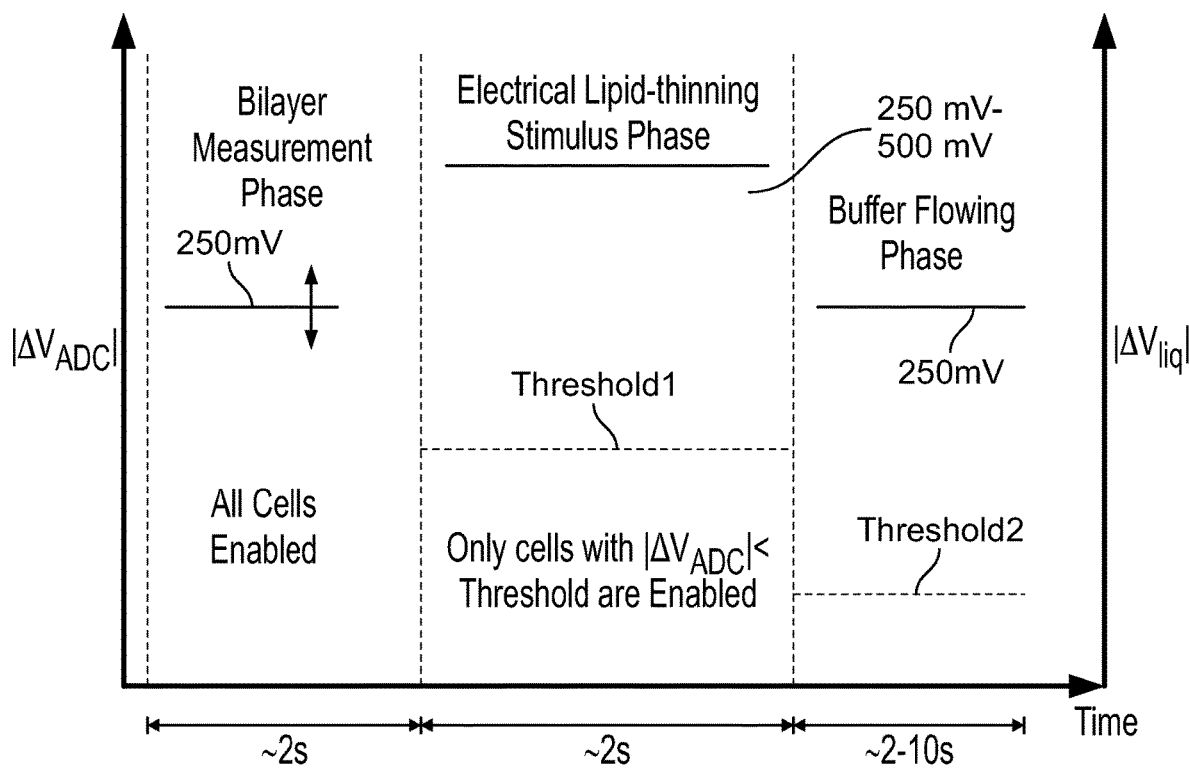
FIG. 13 illustrates an embodiment of a timing diagram for a bilayer measurement phase, an electrical lipid-thinning stimulus phase, and a salt buffer solution flowing phase.

FIG. 13 illustrates an embodiment of a timing diagram for a bilayer measurement phase, an electrical lipid-thinning stimulus phase, and a salt buffer solution flowing phase. In this example, after lipids are deposited into the cells, the bilayer measurement phase is started. The bilayer measurement phase lasts about 2 seconds in time. During this phase, all of the cells are enabled. The absolute value of $V_{liq}$ is 250 mV.

The bilayer measurement phase is followed by the electrical lipid-thinning stimulus phase, which lasts about 2 seconds in time. During this phase, when the absolute value of $\Delta V_{ADC}$ ($|\Delta V_{ADC}|$) exceeds threshold1 within a cell, then a lipid bilayer is detected within the cell and the cell is disconnected from the voltage source. The absolute value of $V_{liq}$ is between 250-500 mV.

The electrical lipid-thinning stimulus phase is followed by the salt buffer solution flowing phase, and the latter lasts about 2-10 seconds in time. During this phase, when the absolute value of $\Delta V_{ADC}$ ($|\Delta V_{ADC}|$) exceeds threshold2 within a cell, then a lipid bilayer is detected within the cell and the cell is disconnected from the voltage source. The absolute value of $V_{liq}$ is 250 mV.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for forming a plurality of lipid bilayers over an array of cells in a nanopore based sequencing chip, the system comprising:
    a nanopore based sequencing chip comprising an array of cells, each of the cells comprising a well;
    a flow chamber coupled to the nanopore based sequencing chip;
    a processor or a circuitry configured to:
        flow a salt buffer solution over the array of cells in the nanopore based sequencing chip to substantially fill the wells in the cells with the salt buffer solution;
        flow a lipid and solvent mixture over the array of cells to deposit the lipid and solvent mixture over at least some of the wells in the cells;
        for each cell of the array of cells, determine whether the cell is covered by a lipid bilayer or a lipid membrane greater than three lipid molecules thick by applying a voltage stimulus and measuring a resultant change in voltage, wherein the cell is covered by a lipid bilayer if the resultant change in voltage is greater than a predetermined threshold or the cell is covered by a lipid membrane greater than three lipid molecules thick if the resultant change in voltage is less than the predetermined threshold; and
        selectively apply a lipid-thinning stimulus to the cells covered by lipid membranes greater than three lipid molecules thick but not to the cells covered by lipid bilayers.

2. The system of claim 1, wherein the lipid-thinning stimulus is an electrical lipid-thinning stimulus.

3. The system of claim 2, wherein the processor or the circuitry is further configured to:
    incrementally increase an absolute magnitude of the electrical lipid-thinning stimulus.

4. The system of claim 3, wherein the processor or the circuitry is further configured to:
    terminate further application of the electrical lipid-thinning stimulus to the array of cells based at least in part on a target yield of the nanopore based sequencing chip, wherein a target yield comprises a target percentage of cells having lipid bilayers over the wells in the cells.

5. The system of claim 2, wherein the processor or the circuitry is further configured to:
    disconnect the cells covered by lipid bilayers from the electrical lipid-thinning stimulus by opening a switch in each of the cells covered by lipid bilayers in order to selectively apply the electrical lipid-thinning stimulus to the cells covered by lipid membranes greater than three lipid molecules thick but not to the cells covered by lipid bilayers.

6. The system of claim 2, wherein the processor or the circuitry is further configured to:
    selectively apply over a first predetermined time period the electrical lipid-thinning stimulus to the cells covered by lipid membranes greater than three lipid molecules thick but not to the cells covered by lipid bilayers;
    during the first predetermined time period, detect that at least one additional cell transitions from having a lipid membrane over its well to having a lipid bilayer over its well; and
    assign the at least one additional cell to the first portion of the cells each having a lipid bilayer over its well without waiting until the first predetermined time period is over, such that the electrical lipid-thinning stimulus is not applied to the at least one additional cell.

7. The system of claim 6, wherein the processor or the circuitry is further configured to:
    after the predetermined time period is over, flow a salt buffer solution over the array of cells in the nanopore based sequencing chip to reduce the thickness of the lipid membranes over the wells in the cells.

8. The system of claim 7, wherein flowing the salt buffer solution over the array of cells in the nanopore based sequencing chip to reduce the thickness of the lipid membranes over the wells in the cells is performed over a second predetermined time period, wherein the processor or the circuitry is further configured to:
    during the second predetermined time period, detect that at least one additional cell transitions from having a lipid membrane over its well to having a lipid bilayer over its well; and
    assign the at least one additional cell to the cells each having a lipid bilayer over its well without waiting until the second predetermined time period is over, such that no electrical stimulus is applied to the at least one additional cell.

9. The system of claim 8, wherein the processor or the circuitry is further configured to:
    repeat a plurality of times the step of selectively applying the electrical lipid-thinning stimulus to the cells covered by lipid membranes greater than three lipid molecules thick but not to the cells covered by lipid bilayers and the step of flowing a salt buffer solution over the array of cells in the nanopore based sequencing chip to reduce the thickness of the lipid membranes over the wells in the cells.

10. A system for forming a plurality of lipid bilayers over an array of cells in a nanopore based sequencing chip, the system comprising:
    a nanopore based sequencing chip comprising an array of cells, each of the cells comprising a well;
    a flow chamber coupled to the nanopore based sequencing chip;
    a processor or a circuitry configured to:
        flow a salt buffer solution over the array of cells in the nanopore based sequencing chip to substantially fill the wells in the cells with the salt buffer solution;
        flow a membrane forming material and solvent mixture over the array of cells to deposit the membrane forming material and solvent mixture over at least some of the wells in the cells;
        detect that a first portion of the cells has a thin membrane over each well by measuring a capacitance of the thin membrane over each well;
        detect that a second portion of the cells has a thick membrane over each well by measuring a capacitance of the thick membrane over each well, wherein the thin membrane is adapted to receive a nanopore and the thick membrane is not adapted to receive a nanopore; and for each cell of the array of cells, determining whether the cell is covered by a thin membrane or a thick membrane, wherein the thin membrane is adapted to receive a nanopore and the thick membrane is not adapted to receive a nanopore, by applying a voltage stimulus and measuring a resultant change in voltage, wherein the cell is covered by a thin membrane if the resultant change in voltage is greater than a predetermined threshold or the cell is covered by a thick membrane if the resultant change in voltage is less than the predetermined threshold; and selectively applying a membrane thinning stimulus to the cells covered by thick membranes but not to the cells covered by thin membranes.

11. The system of claim 10, wherein the membrane thinning stimulus is an electrical membrane thinning stimulus.

12. The system of claim 11, wherein the processor or the circuitry is further configured to:

incrementally increase the absolute magnitude of the electrical membrane thinning stimulus.

13. The system of claim 12, wherein the processor or the circuitry is further configured to:

terminate further application of the electrical membrane thinning stimulus to the array of cells based at least in part on a target yield of the nanopore based sequencing chip, wherein a target yield comprises a target percentage of cells having thin membranes over the wells in the cells.

14. The system of claim 11, wherein the processor or the circuitry is further configured to:

selectively apply the electrical membrane thinning stimulus to the cells covered by thick membranes but not to the cells covered by thin membranes by disconnecting the cells covered by thin membranes from the electrical membrane thinning stimulus by opening a switch in each of the cells covered by thin membranes.

15. The system of claim 11, wherein the processor or the circuitry is further configured to:

selectively apply over a first predetermined time period the electrical membrane thinning stimulus to the cells covered by thick membranes but not to the cells covered by thin membranes;

during the first predetermined time period, detect that at least one additional cell transitions from having a thick membrane over its well to having a thin membrane over its well; and assign the at least one additional cell to the cells each having a thin membrane over its well without waiting until the first predetermined time period is over, such that the electrical membrane thinning stimulus is not applied to the at least one additional cell.

16. The system of claim 15, wherein the processor or the circuitry is further configured to:

after the predetermined time period is over, flow a salt buffer solution over the array of cells in the nanopore based sequencing chip to reduce the thickness of the thick membranes over the wells in the cells.

17. The system of claim 16, wherein flowing the salt buffer solution over the array of cells in the nanopore based sequencing chip to reduce the thickness of the thick membranes over the wells in the cells is performed over a second predetermined time period, wherein the processor or the circuitry is further configured to:

during the second predetermined time period, detect that at least one additional cell transitions from having a thick membrane over its well to having a thin membrane over its well; and assign the at least one additional cell to the cells each having a thin membrane over its well without waiting until the second predetermined time period is over, such that no electrical stimulus is applied to the at least one additional cell.

18. The system of claim 17, wherein the processor or the circuitry is further configured to:

repeat a plurality of times the step of selectively applying the electrical membrane thinning stimulus to the cells covered by thick membranes but not to the cells covered by thin membranes and the step of flowing a salt buffer solution over the array of cells in the nanopore based sequencing chip to reduce the thickness of the thick membranes over the wells in the cells.

* * * * *